(12) United States Patent
Nakatani et al.

(10) Patent No.: US 10,487,355 B2
(45) Date of Patent: Nov. 26, 2019

(54) PCR METHOD AND PCR KIT

(71) Applicant: OSAKA UNIVERSITY, Suita-shi (JP)

(72) Inventors: Kazuhiko Nakatani, Suita (JP); Fumie Sakamoto, Suita (JP)

(73) Assignee: OSAKA UNIVERSITY, Suita-shi (JP)

( * ) Notice: Subject to any disclaimer, the term of this patent is extended or adjusted under 35 U.S.C. 154(b) by 194 days.

(21) Appl. No.: 15/505,480

(22) PCT Filed: Aug. 24, 2015

(86) PCT No.: PCT/JP2015/073755
§ 371 (c)(1),
(2) Date: Feb. 21, 2017

(87) PCT Pub. No.: WO2016/027905
PCT Pub. Date: Feb. 25, 2016

(65) Prior Publication Data
US 2017/0268042 A1    Sep. 21, 2017

(30) Foreign Application Priority Data

Aug. 22, 2014  (JP) .................... 2014-169900

(51) Int. Cl.
*C12Q 1/68* (2018.01)
*C12Q 1/686* (2018.01)
(Continued)

(52) U.S. Cl.
CPC ............. *C12Q 1/686* (2013.01); *C12N 15/09* (2013.01); *C12Q 1/68* (2013.01); *C12Q 1/6818* (2013.01); *C12Q 1/6825* (2013.01); *C12Q 1/6853* (2013.01)

(58) Field of Classification Search
None
See application file for complete search history.

(56) References Cited

U.S. PATENT DOCUMENTS

2010/0015618 A1    1/2010   Nakatani et al.
2014/0255938 A1    9/2014   Nakatani et al.

FOREIGN PATENT DOCUMENTS

JP    2011-182763 A    9/2011
WO   1999/028501 A1   6/1999
(Continued)

OTHER PUBLICATIONS

Takei et al. (Chem Eur J 2007, 13:4452-4457) (Year: 2007).*
(Continued)

*Primary Examiner* — Stephanie K Mummert
(74) *Attorney, Agent, or Firm* — Morrison and Foerster LLP

(57) ABSTRACT

Provided are a PCR method and a PCR kit each of which has higher detection accuracy and is more convenient. A PCR method of the present invention subjects a sample to a PCR reaction, the sample containing: a primer set including a first primer and a second primer; a template amplified by the primer set; a first probe which loses at least one bulge structure in a case where a double strand is formed by the first probe and the first primer and which forms the at least one bulge structure by being dissociated from the double strand formed by the first probe and the first primer; and a bulge structure-binding molecule which emits a signal by binding to the at least one bulge structure.

11 Claims, 17 Drawing Sheets

Specification includes a Sequence Listing.

(51) Int. Cl.
  C12N 15/09    (2006.01)
  C12Q 1/6818   (2018.01)
  C12Q 1/6825   (2018.01)
  C12Q 1/6853   (2018.01)

(56) References Cited

FOREIGN PATENT DOCUMENTS

WO    2008/026582 A1    3/2008
WO    2013/133402 A1    9/2013

OTHER PUBLICATIONS

Chen et al. (Journal of Molecular Diagn, 2013, 15(2):227-233) (Year: 2013).*
Takei et al. (Agnew Chem Int Ed, 2009, 48:7822-7824) (Year: 2009).*
Takei et al. (Chemistry A Eur Journal, 2007, vol. 13, p. 4452-4457, IDS reference) (Year: 2007).*
Gaigai et al, "Development of Fluorescence 'Turn on Type' PCR using Cytosine-Bulge Binding Florescent Molecules", The Proceedings III of 93rd Annual Meeting of the Chemical Society of Japan in Spring (2013), 2 E1-03, 2013, 6 pages (2 pages of English Translation and 4 pages of Official copy).
International Preliminary Report on Patentability received for PCT Application No. PCT/JP2015/073755, dated Mar. 9, 2017, 11 pages (7 pages of English Translation and 4 pages of Official Copy).
International Search Report and Written Opinion received for PCT Patent Application No. PCT/JP2015/073755, dated Nov. 17, 2015, 15 pages (7 pages of English Translation and 8 pages of Official Copy).
Takei et al, "Competitive Allele-Specific Hairpin Primer PCR for Extremely High Allele Discrimination in Typing of Single Nucleotide Polymorphisms", ChemBioChem, vol. 13, 2012, pp. 1409-1412.
Takei et al, "Cytosine-Bulge-Dependent Fluorescence Quenching for the Real-Time Hairpin Primer PCR", Chem Commun, vol. 50, 2014, pp. 15195-15198.
Takei et al, "Development of the Signal-on Type of Polymerase Chain Reaction System using Cytosine-Bulge Hairpin Probe", Proceedings III of 95th Annual Meeting of the Chemical Society of Japan in Spring (2015),1 J6-36, 2015,6 pages (2 pages of English Translation and 4 pages of official copy).
Takei et al, "Secondary-Structure-Inducible Ligand Fluorescence Coupled with PCR", Angew. Chem. Int. Ed., vol. 48, 2009, pp. 7822-7824.
Chen et al., "A Novel DANP-Coupled Hairpin RT-PCR for Rapid Detection of Chikungunya Virus", The Journal of Molecular Diagnostics, vol. 15, No. 2, Mar. 2013, pp. 227-233.
Extended European Search Report received for European Patent Application No. 15833348.4, dated Jan. 2, 2018, 7 pages.
Nakatani, Kazuhiko, "Chemistry Challenges in SNP Typing", ChemBioChem, vol. 5, 2004, pp. 1623-1633.
Suda et al., "N,N'-Bis(3-Aminopropyl)-2,7-Diamino-1,8-Naphthyridine Stabilized a Single Pyrimidine Bulge in Duplex DNA", Bioorganic & Medicinal Chemistry, vol. 13, 2005, pp. 4507-4512.
Takei et al., "Allele Specific C-Bulge Probes with One Unique Fluorescent Molecule Discriminate the Single Nucleotide Polymorphism in DNA", Chemistry-A European Journal, vol. 13, 2007, pp. 4452-4457.
Takei et al., "Detection of Hepatitis C Virus by Single-Step Hairpin Primer RT-PCR", Bioorganic & Medicinal Chemistry Letters, vol. 24, 2014, pp. 394-396.
Takei et al., "Fluorescence Turn-on Hairpin-Probe PCR", Chemical Communications, vol. 53, 2017, pp. 1393-1396.

* cited by examiner

```
Probe :
Short C+2 : 3' -ctcTAGTA_ATGTCTGttttCA_ACATCTACTA- 5'

Reverse primer :
Short TAG+1 : 5' -AGACAAAAGTTGTAGATGATTTCACAGGAAACAGCTATGAC-3'

Forward primer :
Short tag1-M13M3 : 5' -AGACAAAAGTTGTAGATGATTTCAGTTGTAAAACGACGGCCAGT-3'
```

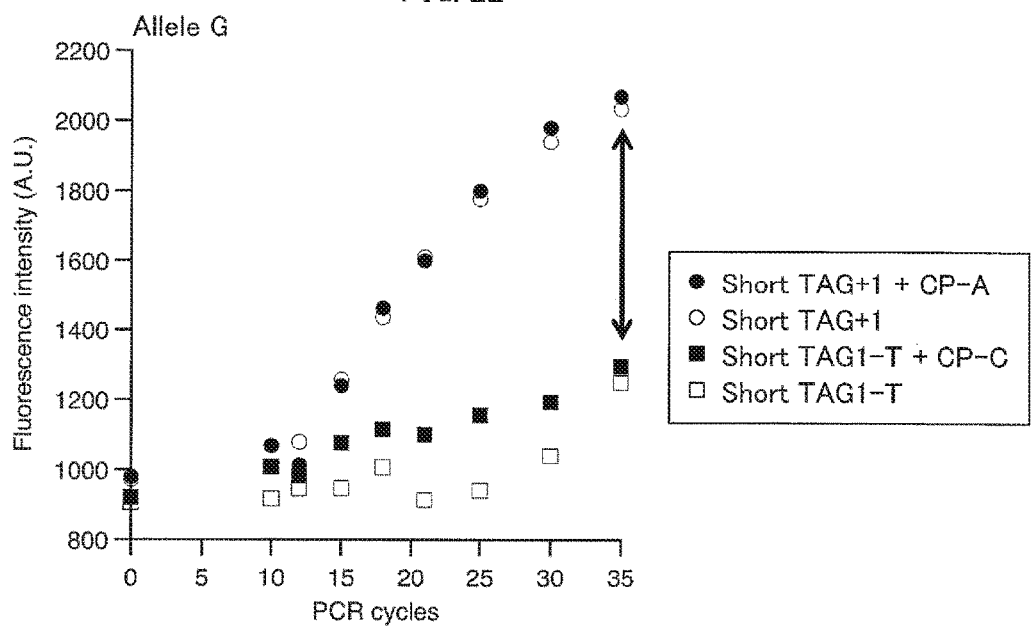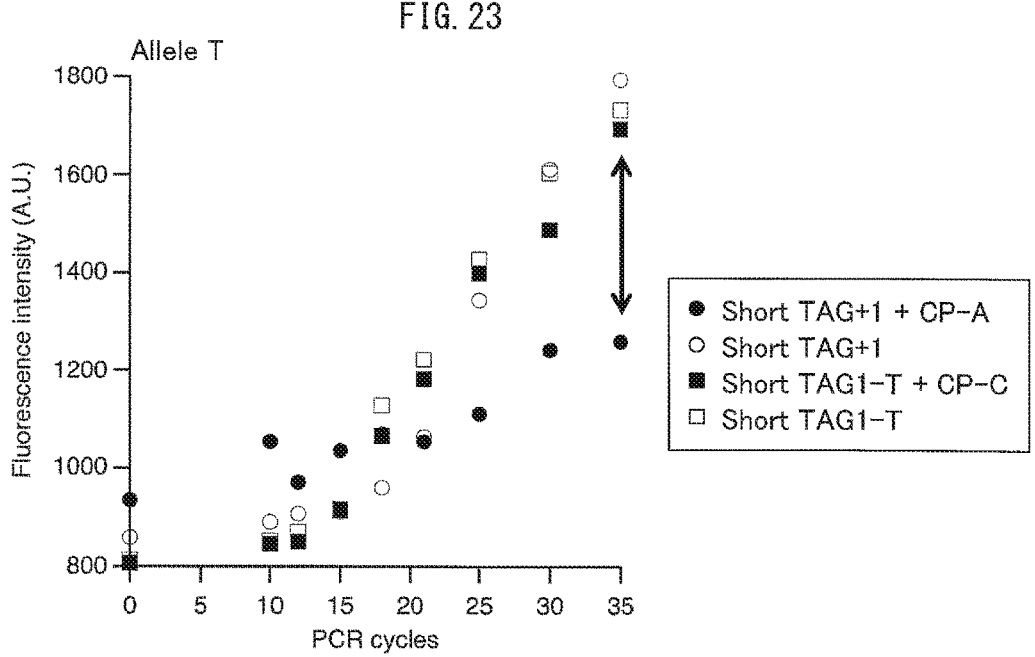

SEQUENCE LISTING

<160> NUMBER OF SEQ ID NOS: 24

<210> SEQ ID NO 1
<211> LENGTH: 20
<212> TYPE: DNA
<213> ORGANISM: Artificial Sequence
<220> FEATURE:
<223> OTHER INFORMATION: Synthetic Construct

<400> SEQUENCE: 1
gttgtaaaac gacggccagt                      20

<210> SEQ ID NO 2
<211> LENGTH: 41
<212> TYPE: DNA
<213> ORGANISM: Artificial Sequence
<220> FEATURE:
<223> OTHER INFORMATION: Synthetic Construct

<400> SEQUENCE: 2
tcattacaaa agtagatgat ttcacaggaa acagctatga c                      41

<210> SEQ ID NO 3
<211> LENGTH: 24
<212> TYPE: DNA
<213> ORGANISM: Artificial Sequence

```
<220> FEATURE:
<223> OTHER INFORMATION: Synthetic Construct

<400> SEQUENCE: 3
atcatctact tttgtaatga tctc                                              24

<210> SEQ ID NO 4
<211> LENGTH: 43
<212> TYPE: DNA
<213> ORGANISM: Artificial Sequence
<220> FEATURE:
<223> OTHER INFORMATION: Synthetic Construct

<400> SEQUENCE: 4
gctatcaaaa gaagctatct atttcacagg aaacagctat gac                         43

<210> SEQ ID NO 5
<211> LENGTH: 31
<212> TYPE: DNA
<213> ORGANISM: Artificial Sequence
<220> FEATURE:
<223> OTHER INFORMATION: Synthetic Construct

<400> SEQUENCE: 5
atagatagct tcttttgata gcttctatct c                                      31

<210> SEQ ID NO 6
<211> LENGTH: 40
<212> TYPE: DNA
<213> ORGANISM: Artificial Sequence
<220> FEATURE:
<223> OTHER INFORMATION: Synthetic Construct

<400> SEQUENCE: 6
gtagatgata atacgtcact tcacaggaaa cagctatgac                             40

<210> SEQ ID NO 7
<211> LENGTH: 41
<212> TYPE: DNA
<213> ORGANISM: Artificial Sequence
<220> FEATURE:
<223> OTHER INFORMATION: Synthetic Construct

<400> SEQUENCE: 7
gtgacgtatt atcatctaca acttttgtct gtaatgatct c                           41

<210> SEQ ID NO 8
<211> LENGTH: 39
<212> TYPE: DNA
<213> ORGANISM: Artificial Sequence
<220> FEATURE:
<223> OTHER INFORMATION: Synthetic Construct

<400> SEQUENCE: 8
tagatgataa tacgtcactt cacaggaaac agctatgac                              39

<210> SEQ ID NO 9
<211> LENGTH: 40
<212> TYPE: DNA
<213> ORGANISM: Artificial Sequence
<220> FEATURE:
<223> OTHER INFORMATION: Synthetic Construct

<400> SEQUENCE: 9
gtagatgata atacgtcact tcacaggaaa cagctatgac                             40
```

<210> SEQ ID NO 10
<211> LENGTH: 41
<212> TYPE: DNA
<213> ORGANISM: Artificial Sequence
<220> FEATURE:
<223> OTHER INFORMATION: Synthetic Construct

<400> SEQUENCE: 10
tgtagatgat aatacgtcac ttcacaggaa acagctatga c                41

<210> SEQ ID NO 11
<211> LENGTH: 42
<212> TYPE: DNA
<213> ORGANISM: Artificial Sequence
<220> FEATURE:
<223> OTHER INFORMATION: Synthetic Construct

<400> SEQUENCE: 11
ttgtagatga taatacgtca cttcacagga aacagctatg ac               42

<210> SEQ ID NO 12
<211> LENGTH: 43
<212> TYPE: DNA
<213> ORGANISM: Artificial Sequence
<220> FEATURE:
<223> OTHER INFORMATION: Synthetic Construct

<400> SEQUENCE: 12
acagacaaaa gttgtagatg atttcacagg aaacagctat gac              43

<210> SEQ ID NO 13
<211> LENGTH: 42
<212> TYPE: DNA
<213> ORGANISM: Artificial Sequence
<220> FEATURE:
<223> OTHER INFORMATION: Synthetic Construct

<400> SEQUENCE: 13
cagacaaaag ttgtagatga tttcacagga aacagctatg ac               42

<210> SEQ ID NO 14
<211> LENGTH: 41
<212> TYPE: DNA
<213> ORGANISM: Artificial Sequence
<220> FEATURE:
<223> OTHER INFORMATION: Synthetic Construct

<400> SEQUENCE: 14
agacaaaagt tgtagatgat ttcacaggaa acagctatga c                41

<210> SEQ ID NO 15
<211> LENGTH: 40
<212> TYPE: DNA
<213> ORGANISM: Artificial Sequence
<220> FEATURE:
<223> OTHER INFORMATION: Synthetic Construct

<400> SEQUENCE: 15
gacaaaagtt gtagatgatt tcacaggaaa cagctatgac                  40

<210> SEQ ID NO 16
<211> LENGTH: 39
<212> TYPE: DNA
<213> ORGANISM: Artificial Sequence
<220> FEATURE:
<223> OTHER INFORMATION: Synthetic Construct

<400> SEQUENCE: 16
acaaaagttg tagatgattt cacaggaaac agctatgac                                      39

<210> SEQ ID NO 17
<211> LENGTH: 38
<212> TYPE: DNA
<213> ORGANISM: Artificial Sequence
<220> FEATURE:
<223> OTHER INFORMATION: Synthetic Construct

<400> SEQUENCE: 17
caaaagttgt agatgatttc acaggaaaca gctatgac                                       38

<210> SEQ ID NO 18
<211> LENGTH: 37
<212> TYPE: DNA
<213> ORGANISM: Artificial Sequence
<220> FEATURE:
<223> OTHER INFORMATION: Synthetic Construct

<400> SEQUENCE: 18
aaaagttgta gatgatttca caggaaacag ctatgac                                        37

<210> SEQ ID NO 19
<211> LENGTH: 36
<212> TYPE: DNA
<213> ORGANISM: Artificial Sequence
<220> FEATURE:
<223> OTHER INFORMATION: Synthetic Construct

<400> SEQUENCE: 19
aaagttgtag atgatttcac aggaaacagc tatgac                                         36

<210> SEQ ID NO 20
<211> LENGTH: 31
<212> TYPE: DNA
<213> ORGANISM: Artificial Sequence
<220> FEATURE:
<223> OTHER INFORMATION: Synthetic Construct

<400> SEQUENCE: 20
atcatctaca acttttgtct gtaatgatct c                                              31

<210> SEQ ID NO 21
<211> LENGTH: 44
<212> TYPE: DNA
<213> ORGANISM: Artificial Sequence
<220> FEATURE:
<223> OTHER INFORMATION: Synthetic Construct

<400> SEQUENCE: 21
agacaaaagt tgtagatgat ttcagttgta aaacgacggc cagt                                44

<210> SEQ ID NO 22
<211> LENGTH: 20
<212> TYPE: DNA
<213> ORGANISM: Artificial Sequence
<220> FEATURE:
<223> OTHER INFORMATION: Synthetic Construct

<400> SEQUENCE: 22
acacaggaaa cagctatgaa                                                           20

<210> SEQ ID NO 23

```
<211> LENGTH: 41
<212> TYPE: DNA
<213> ORGANISM: Artificial Sequence
<220> FEATURE:
<223> OTHER INFORMATION: Synthetic Construct

<400> SEQUENCE: 23
agacaaaagt gtagatgat ttcacaggaa acagctatga a            41

<210> SEQ ID NO 24
<211> LENGTH: 19
<212> TYPE: DNA
<213> ORGANISM: Artificial Sequence
<220> FEATURE:
<223> OTHER INFORMATION: Synthetic Construct

<400> SEQUENCE: 24
cacaggaaac agctatgac                                    19
```

PCR METHOD AND PCR KIT

CROSS-REFERENCE TO RELATED APPLICATIONS

This application is a U.S. National Phase patent application of International Patent Application No. PCT/JP2015/073755, filed Aug. 24, 2015, which claims priority to Japanese Application No. 2014-169900, filed Aug. 22, 2014, each of which is hereby incorporated by reference in the present disclosure in its entirety.

SUBMISSION OF SEQUENCE LISTING ON ASCII TEXT FILE

The content of the following submission on ASCII text file is incorporated herein by reference in its entirety: a computer readable form (CRF) of the Sequence Listing (file name: 247322019900SeqList.txt, date recorded: Feb. 21, 2017, size: 5 KB).

FIELD OF THE INVENTION

The present invention relates to a PCR method and a PCR kit.

BACKGROUND OF THE INVENTION

Examples of a real time polymerase chain reaction (real time PCR) method that is widely used to detect a gene include a TaqMan (Registered Trademark) method and an SYBR (Registered Trademark) Green method.

The TaqMan (Registered Trademark) method, which is an extremely highly sensitive method, has (i) a problem of complexity of designing and synthesis of a probe for use in detection and (ii) a problem of high detection cost.

Meanwhile, the SYBR (Registered Trademark) Green method is a convenient method using a pigment that increases in fluorescence intensity when bound to a double-stranded DNA. Note, however, that according to the SYBR (Registered Trademark) Green method, a nonspecifically amplified double-stranded DNA will also be detected as "positive. In view of this, the SYBR (Registered Trademark) Green method has a problem of causing a great error in detection. Further, the SYBR (Registered Trademark) Green method also has a problem of difficulty in designing of a primer having high detection accuracy.

In order that the problems of the TaqMan (Registered Trademark) method and of the SYBR (Registered Trademark) Green method will be solved, new PCR methods have been developed so far (see, for example, Patent Literature 1).

The following description discusses, with reference to FIG. 26, a basic concept of a technique disclosed in Patent Literature 1.

The technique disclosed in Patent Literature 1 uses a primer that is capable of forming a double strand in a molecule and is also capable of forming a cytosine bulge structure in the double strand, the primer emitting fluorescence in response to binding of 2,7-diamino-1,8-naphthyridine (DANP) to the cytosine bulge structure. Note that a cytosine bulge structure is a characteristic structure formed by cytosine with which no complementary nucleotide is to be paired.

Before a PCR reaction is started, DANP binds to the cytosine bulge structure in the primer, and intense fluorescence is emitted (see (d) of FIG. 26).

After the PCR reaction is started, first, the primer binds to a template, and a complementary strand of the template is extended from the primer (see (a) of FIG. 26).

Next, a double strand formed by the complementary strand and the template is separated, by a high temperature treatment, into (a) a single strand including the complementary strand (hereinafter referred to as a "single strand A") and (b) a single strand including the template.

Subsequently, another primer (not illustrated in FIG. 26) binds to the single strand A, and the complementary strand of the single strand A is extended from the another primer (see (b) of FIG. 26).

During a process in which the complementary strand of the single strand A is extended, a complementary nucleotide corresponding to the cytosine is formed in the complementary strand of the single strand A. This results in a loss of the cytosine bulge structure (see (c) of FIG. 26).

According to the technique disclosed in Patent Literature 1, the number of cytosine bulge structures decreases as the PCR reaction progresses, so that a fluorescence intensity is reduced (see (d) of FIG. 26). According to the technique disclosed in Patent Literature 1, the PCR reaction is detected by observing a reduction in fluorescence intensity.

CITATION LIST

[Patent Literature 1]
WO2008/026582 A1 (Publication Date: Mar. 6, 2008)

SUMMARY OF THE INVENTION

The conventional technique (described earlier) is a technique that has sufficient detection accuracy and is convenient. Note, however, that the conventional technique is demanded to have higher detection accuracy and be more convenient.

For example, the conventional technique (described earlier) needs to use a long primer to form a bulge structure. This makes it impossible to deny the possibility that the long primer may nonspecifically bind to a template and consequently cause amplification of a nonspecific gene.

Further, the conventional technique (described earlier), which is a method for detecting a PCR reaction by measuring an amount of reduction in fluorescence intensity, has a narrow dynamic range and thus tends to have low detection accuracy.

The present invention has been made in view of the above conventional problems, and an object of the present invention is to provide a PCR method and a PCR kit each of which has higher detection accuracy and is more convenient.

In order to attain the object, a PCR method of an aspect of the present invention includes the step of: subjecting a sample to a PCR reaction, the sample containing: a primer set including a first primer and a second primer; a template amplified by the primer set; a first probe which loses at least one bulge structure in a case where a double strand is formed by the first probe and the first primer and which forms the at least one bulge structure by being dissociated from the double strand formed by the first probe and the first primer; and a bulge structure-binding molecule which emits a signal by binding to the at least one bulge structure.

The PCR method of an aspect of the present invention is preferably arranged such that: the first probe has a first polynucleotide sequence and a second polynucleotide sequence which form a double strand with each other by use of nucleotides different from a nucleotide forming the at least one bulge structure, and the first probe has a third polynucleotide sequence with which a part of the first primer forms a double strand; and the third polynucleotide sequence includes at least a part of the first polynucleotide sequence or the second polynucleotide sequence.

The PCR method of an aspect of the present invention is preferably arranged such that $Tm_1 > Tm_2$ where a melting temperature of the double strand formed by the third polynucleotide sequence and the first primer is $Tm_1$ and a melting temperature of the double strand formed by the first polynucleotide sequence and the second polynucleotide sequence is $Tm_2$.

The PCR method of an aspect of the present invention is preferably arranged such that the at least one bulge structure formed by the first probe comprises a plurality of bulge structures.

The PCR method of an aspect of the present invention is preferably arranged such that the sample further contains a second probe which loses at least one bulge structure in a case where a double strand is formed by the second probe and the second primer and which forms the at least one bulge structure by being dissociated from the double strand formed by the second probe and the second primer.

The PCR method of an aspect of the present invention is preferably arranged such that: the second probe has a fourth polynucleotide sequence and a fifth polynucleotide sequence which form a double strand with each other by use of nucleotides different from a nucleotide forming the at least one bulge structure, and the second probe has a sixth polynucleotide sequence with which a part of the second primer forms a double strand; and the sixth polynucleotide sequence includes at least a part of the fourth polynucleotide sequence or the fifth polynucleotide sequence.

The PCR method of an aspect of the present invention is preferably arranged such that $Tm_3 > Tm_4$ where a melting temperature of the double strand formed by the sixth polynucleotide sequence and the second primer is $Tm_3$ and a melting temperature of the double strand formed by the fourth polynucleotide sequence and the fifth polynucleotide sequence is $Tm_4$.

The PCR method of an aspect of the present invention is preferably arranged such that the at least one bulge structure formed by the second probe comprises a plurality of bulge structures.

The PCR method of an aspect of the present invention is preferably arranged such that the at least one bulge structure is a cytosine bulge structure or a thymine bulge structure.

The PCR method of an aspect of the present invention is preferably arranged such that the bulge structure-binding molecule is a naphthyridine ring-containing compound.

The PCR method of an aspect of the present invention is preferably arranged such that: the sample further contains a competitor primer; and the competitor primer has a seventh polynucleotide sequence that corresponds to a region of the first primer in which region a double strand is formed by the first primer and the template and at least one nucleotide is replaced with another nucleotide.

In order to attain the object, a PCR kit of an aspect of the present invention for causing a primer set including a first primer and a second primer to amplify a template, the PCR kit includes: a first probe which loses at least one bulge structure in a case where a double strand is formed by the first probe and the first primer and which forms the at least one bulge structure by being dissociated from the double strand formed by the first probe and the first primer; and a bulge structure-binding molecule which emits a signal by binding to the at least one bulge structure.

A PCR kit of an aspect of the present invention is preferably arranged to further include: a second probe which loses at least one bulge structure in a case where a double strand is formed by the second probe and the second primer and which forms the at least one bulge structure by being dissociated from the double strand formed by the second probe and the second primer.

A PCR kit of an aspect of the present invention is preferably arranged to further include: a competitor primer having a seventh polynucleotide sequence that corresponds to a region of the first primer in which region a double strand is formed by the first primer and the template and at least one nucleotide is replaced with another nucleotide.

An aspect of the present invention is a technique for detecting an increasing intensity of a signal (e.g., fluorescence). Thus, as compared with a technique for detecting a decreasing signal intensity, an aspect of the present invention yields an effect of allowing easier and more accurate understanding of how a PCR reaction progresses (e.g., an amount of a product of the PCR reaction).

Specifically, an aspect of the present invention makes it unnecessary to electrophorese a PCR product and thus makes it possible to easily understand how the PCR reaction progresses.

According to the technique for detecting a decreasing signal intensity, a decreasing signal intensity is measured based on a strong signal that is already present (i.e., a high background). Therefore, the technique for detecting a decreasing signal intensity makes it difficult to accurately measure a decreasing signal intensity and thus makes it difficult to accurately understand how the PCR reaction progresses. In particular, in a case where a decreasing signal intensity is low, the technique for detecting a decreasing signal intensity makes it difficult to understand how the PCR reaction progresses.

Meanwhile, according to an aspect of the present invention, an increasing signal intensity is measured based on a signal that is absent (i.e., a low background). Therefore, an aspect of the present invention makes it easy to accurately measure an increasing signal intensity and thus makes it easy to accurately understand how the PCR reaction progresses. According to an aspect of the present invention, even in a case where an increasing signal intensity is low, it is possible to accurately understand how the PCR reaction progresses.

Further, an aspect of the present invention yields an effect of being highly versatilely available for any gene.

Specifically, according to an aspect of the present invention, it is only necessary to attach, to any primer for detecting any gene, a tag that is capable of changing a bulge structure of a probe by binding to the probe. Therefore, an aspect of the present invention can be used for a PCR that is targeted at any gene.

An aspect of the present invention makes it unnecessary to use a probe and a primer each subjected to chemical modification (e.g., fluorescence modification). Thus, an aspect of the present invention yields an effect of achieving the probe and the primer each of which is easily synthesized and is inexpensive.

An aspect of the present invention, which aspect requires no special device, yields an effect of being carried out by use of a conventional device (e.g., a PCR device, a fluorescence detecting device).

Further, by capping a 3' end of a probe with a non-native DNA, a DNA is not amplified by the probe even in a case where the probe binds to an unintended sequence. That is, it is possible to prevent the probe from functioning as a primer.

For example, in a case where dideoxyribose is located at the 3' end of the probe, since dideoxyribose has no "—OH" that is necessary for an extension reaction, it is possible to prevent the probe from functioning as a primer.

BRIEF DESCRIPTION OF THE DRAWINGS

FIG. 22 is a graph showing a result of fluorescence analysis carried out in the further example of an aspect of the present invention by use of a template whose allele is "G".

FIG. 23 is a graph showing a result of fluorescence analysis carried out in the further example of an aspect of the present invention by use of a template whose allele is "T".

DESCRIPTION OF THE INVENTION

The description below deals with an embodiment of the present invention. Note, however, that the present invention is not limited to the embodiment. The present invention is not limited to the description of the arrangements below but may be altered in various ways within the scope of the claims. Any embodiment or example based on a proper combination of technical means disclosed in different embodiments and examples is also encompassed in the technical scope of the present invention.

All academic and patent literatures listed herein are incorporated herein by reference. Unless otherwise specified herein, any numerical range expressed as "A to B" means "not less than A (A or more) and not more than B (B or less)".

[1. Fundamental Principle of Aspect of the Present Invention]

First, a fundamental principle of an aspect of the present invention will be described with reference to FIG. 1.

Figure 1:
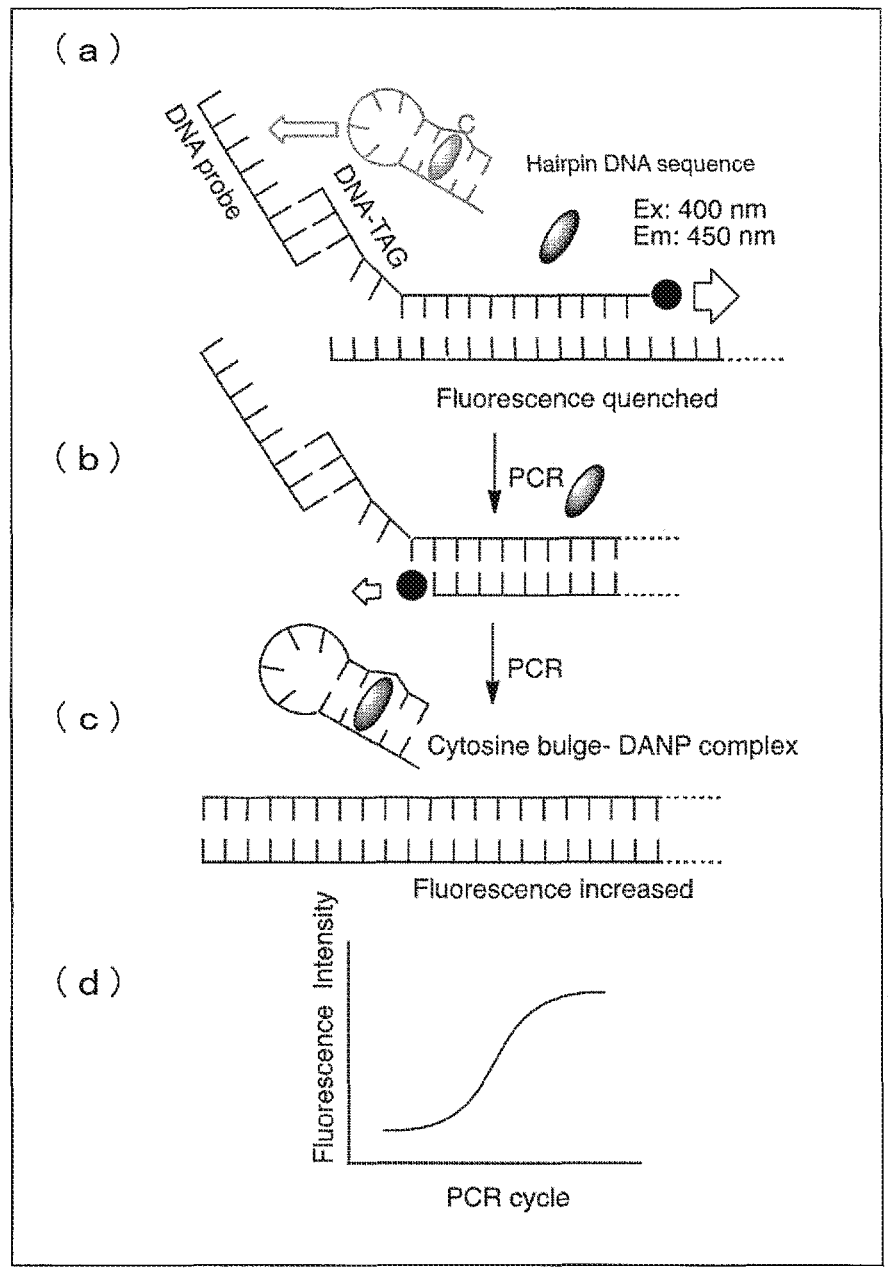
FIG. 1 illustrates a fundamental principle of an aspect of the present invention.

An aspect of the present invention uses a probe that is capable of forming a bulge structure in a molecule and emits a signal (e.g., fluorescence) in response to binding of a bulge structure-binding molecule to the bulge structure (see DNA probe of FIG. 1).

A "bulge structure" herein means a bulge that occurs due to presence of an excess nucleotide in one of polynucleotide single strands contained in a polynucleotide (e.g., DNA) double strand.

For example, in a case where "TCT" and "AA" face each other so as to form a double strand, two "T"s of "TCT" and respective two "A"s of "AA" are paired so as to form the double strand. In this case, "C", which is present between the two "T"s, has no nucleotide to be paired with. Thus, the "C" bulges. Such a structure of the "C" thus bulging is a bulge structure.

Note that as in the example described above, a bulge structure that is formed in a case where an excess base is C (cytosine) is herein referred to as a "cytosine bulge structure". As in the case of C (cytosine), a bulge structure that is formed in a case where an excess base is A (adenine) is herein referred to as an "adenine bulge structure", a bulge structure that is formed in a case where an excess base is G (guanine) is herein referred to as a "guanine bulge structure", and a bulge structure that is formed in a case where an excess base is T (thymine) is herein referred to as a "thymine bulge structure".

When a PCR reaction is started, a conformation of the probe is changed by binding between the probe and a primer (see DNA-TAG of FIG. 1), so that a bulge structure in the probe is lost. Thus, no signal that is derived from a bulge structure-binding molecule is emitted when the PCR reaction is started (see (d) of FIG. 1).

After the PCR reaction is started, first, a complex of the probe and the primer binds to a template, and a complementary strand of the template is extended from the primer (see (a) of FIG. 1).

Next, a double strand formed by the complementary strand and the template is separated, by a high temperature treatment, into (a) a strand including at least the complementary strand (hereinafter referred to as a "strand B") and (b) a single strand including the template.

Subsequently, another primer (not illustrated in FIG. 1) binds to the strand B, and the complementary strand of the strand B is extended from the primer (see (b) of FIG. 1).

During a process in which the complementary strand of the strand B is extended, a complementary nucleotide corresponding to a region of the probe in which region the primer binds to the probe is formed in the complementary strand of the strand B. As a result, the probe which has lost an object to bind to is dissociated in a PCR reaction solution (see (c) of FIG. 1).

The probe which has been dissociated in the PCR reaction solution forms a bulge structure therein due to an interaction between regions of the probe via, for example, a hydrogen bond in a molecule of the probe. Further, a bulge structure-binding molecule binds to the bulge structure. As a result, a signal (e.g., fluorescence) is emitted (see (c) of FIG. 1).

According to an aspect of the present invention, the number of probes dissociated (i.e., the number of bulge structures) increases as the PCR reaction progresses, so that a signal intensity increases (see (d) of FIG. 1). According to an aspect of the present invention, the PCR reaction is detected by observing an increase in signal intensity. Note that an aspect of the present invention, which aspect has a broad dynamic range, makes it possible to achieve a PCR method having high detection accuracy.

A PCR method of the present embodiment includes the step of: subjecting a sample to a PCR reaction, the sample containing: a primer set including a first primer and a second primer; a template amplified by the primer set; a first probe whose at least one structure (specifically, bulge structure) is changed in accordance with how the first probe binds to the first primer; and a bulge structure-binding molecule that changes, in accordance with how the bulge structure-binding molecule binds to the at least one bulge structure, a signal to emit.

The following description discusses arrangements of the present invention.

The first probe loses at least one bulge structure in a case where a double strand is formed by the first probe and the first primer, and the first probe forms the at least one bulge structure by being dissociated from the double strand formed by the first probe and the first primer (specifically, the first probe is a polynucleotide (e.g., a DNA)).

That is, the first probe which is solely present forms therein the at least one bulge structure, and a conformation of the first probe is changed in a case where the double strand is formed by the first probe and the first primer, so that the at least one bulge structure is lost.

The first probe only needs to have the property described above, and a base sequence of the first probe is not limited to a specific one.

More specifically, the first probe may have a first polynucleotide sequence and a second polynucleotide sequence which form a double strand with each other by use of nucleotides different from a nucleotide forming the at least one bulge structure.

In this case, the first polynucleotide sequence and the second polynucleotide sequence may be arranged such that the nucleotides different from the nucleotide forming the at least one bulge structure are wholly complementary or partly complementary.

Note that "complementary" herein means a relationship in which adenine (A) and thymine (T) face each other via a specific hydrogen bond and guanine (G) and cytosine (C) face each other via a specific hydrogen bond.

More specifically, the first polynucleotide sequence and the second polynucleotide sequence can be arranged such that not less than 50%, preferably not less than 60%, more preferably not less than 70%, more preferably not less than 80%, more preferably not less than 90%, more preferably not less than 95%, more preferably not less than 98%, and most preferably 100% of the nucleotides different from the nucleotide forming the at least one bulge structure are complementary.

With the arrangement, the first polynucleotide sequence and the second polynucleotide sequence form the double strand in the first probe via a specific hydrogen bond. An excess nucleotide with which no nucleotide is to be paired forms the at least one bulge structure.

The first probe preferably has a third polynucleotide sequence with which a part of the first primer forms a double strand.

In this case, the part of the first primer and the third polynucleotide sequence may be wholly complementary or may be partly complementary.

More specifically, the part of the first primer and the third polynucleotide sequence can be arranged such that not less than 50%, preferably not less than 60%, more preferably not less than 70%, more preferably not less than 80%, more preferably not less than 90%, more preferably not less than 95%, more preferably not less than 98%, and most preferably 100% of nucleotides forming the double strand are complementary.

The arrangement allows the first probe and the part of the first primer to form a double strand via the third polynucleotide sequence. In a case where the double strand is formed by the first probe and the first primer via the third polynucleotide sequence, a conformation of the first probe is changed, so that a bulge structure in the first primer is lost. Note that a part of the first primer in which part no double strand is formed by the first primer and the first probe functions in a case where a double strand is formed by the first primer and the template.

The third polynucleotide sequence preferably includes at least a part of the first polynucleotide sequence or the second polynucleotide sequence. The third polynucleotide may include a whole of the first polynucleotide sequence or the second polynucleotide sequence.

With the arrangement, in a case where a double strand is formed by binding between the first primer and the third polynucleotide, the binding between the first primer and the third polynucleotide makes it possible to effectively inhibit formation of a double strand by binding between the first polynucleotide sequence and the second polynucleotide sequence. As a result, the arrangement allows detection of a PCR with higher accuracy by reducing a background of a signal.

A base sequence of each of the first polynucleotide sequence, the second polynucleotide sequence, and the third polynucleotide sequence is not particularly limited to a specific one. The first polynucleotide sequence, the second polynucleotide sequence, and the third polynucleotide sequence each can be appropriately designed to have a desired base sequence.

For example, it is preferable to design the base sequence of each of the first polynucleotide sequence, the second polynucleotide sequence, and the third polynucleotide so that a relational expression "$Tm_1 > Tm_2$" where a melting temperature of the double strand formed by the third polynucleotide sequence and the first primer is $Tm_1$ and a melting temperature of the double strand formed by the first polynucleotide sequence and the second polynucleotide sequence is $Tm_2$ is satisfied. Note that a melting temperature can be calculated by use of a well-known calculation program such as OligoCalc (Inc50 mM Na$^+$, "available at the website www.basic.northwestern.edu at biotools/oligocalc.html").

With the arrangement, the double strand formed by the third polynucleotide sequence and the first primer is made more stable than the double strand formed by the first polynucleotide sequence and the second polynucleotide sequence. That is, the double strand formed by the third polynucleotide sequence and the first primer is more preferentially formed than the double strand formed by the first polynucleotide sequence and the second polynucleotide sequence, and a noise of the signal is reduced. As a result, as proved in Examples (described later), the arrangement allows detection of a PCR with higher accuracy.

More specifically, the first polynucleotide sequence, the second polynucleotide sequence, and the third polynucleotide sequence each preferably have the base sequence which is designed so that a relational expression "$Tm_1 > Tm_2 >$ signal measurement temperature" is satisfied. Note that a signal measurement temperature (e.g., a fluorescence measurement temperature) is not particularly limited to a specific one and can be, for example, 25° C. or 30° C.

The arrangement does not inhibit formation of the double strand in the first probe (i.e., emission of fluorescence) during signal measurement and thus allows detection of a PCR with higher accuracy.

The base sequence of each of the first polynucleotide sequence and the second polynucleotide sequence can be designed so that one or more (e.g., 2 to 4) bulge structures are formed in the first probe. From the viewpoint of allowing detection of a PCR with higher accuracy by increasing a signal intensity, the base sequence of each of the first polynucleotide sequence and the second polynucleotide sequence is more preferably designed so that a plurality of bulge structures is formed.

In a case where a plurality of bulge structures is formed in the first probe, preferably 2 to 5, and more preferably 3 to 4 bases are present between adjacent bulge structures of the plurality of bulge structures. A too short distance between bulge structures prevents a bulge structure-binding molecule from satisfactorily binding to each of the bulge structures, so that a signal intensity tends to decrease. Meanwhile, a too long distance between bulge structures makes an overall length of the first probe long, so that cost of preparation of the first probe tends to increase.

A bulge structure that is formed in the first probe is not particularly limited to a specific one. Examples of the bulge structure include a cytosine bulge structure, a thymine bulge structure, an adenine bulge structure, and a guanine bulge structure.

From the viewpoint of allowing detection of a PCR with higher accuracy by increasing a signal intensity, the bulge structure is preferably the cytosine bulge structure, the thymine bulge structure, or the adenine bulge structure, more preferably the cytosine bulge structure or the thymine bulge structure, and most preferably the cytosine bulge structure.

A nucleotide that is adjacent to the bulge structure is not particularly limited in kind and is preferably adenine, cytosine, or thymine. In a case where the bulge structure-binding molecule is a molecule that emits fluorescence, the fluorescence tends to have a lower intensity when guanine is adjacent to the bulge structure, whereas the fluorescence tends to have a higher intensity when adenine, cytosine, or thymine is adjacent to the bulge structure.

The first polynucleotide sequence and the second polynucleotide sequence each have a length (i.e., the number of nucleotides forming a polynucleotide) that is not particularly limited and is, for example, preferably 7 to 17 nucleotides, more preferably 8 to 17 nucleotides, and still more preferably 8 to 12 nucleotides. For example, in a case where the first polynucleotide sequence and the second polynucleotide sequence are each formed of 17 nucleotides, three or more bulge structures can be formed.

The arrangement makes it possible to achieve a probe that is capable of forming a stable bulge structure and to achieve an inexpensive probe.

The third polynucleotide sequence has a length (i.e., the number of nucleotides forming a polynucleotide) that is not particularly limited and is, for example, preferably 17 to 25 nucleotides, and more preferably 18 to 22 nucleotides.

The arrangement makes it possible to effectively inhibit a probe from forming a bulge structure and thus allows detection of a PCR with higher accuracy.

The first probe may be arranged such that one or more (e.g., 3 to 7, preferably 4) nucleotides are present between the first polynucleotide sequence and the second polynucleotide sequence. Such a nucleotide is not particularly limited in kind and is preferably thymine.

The arrangement makes it possible to change a structure of the first probe into a desired structure (e.g., a single strand or a hairpin structure).

The first probe preferably has a 3' end that is capped with a non-native DNA. With the arrangement, a DNA is not amplified by the first probe even in a case where the first probe binds to an unintended sequence. That is, since the first probe does not function as a primer, it is possible to prevent the first probe from nonspecifically amplifying a DNA.

For example, in a case where dideoxyribose is located at the 3' end of the first probe, since dideoxyribose has no "—OH" that is necessary for an extension reaction, it is possible to prevent the first probe from functioning as a primer.

The primer set includes the first primer (e.g., reverse primer) and the second primer (e.g., a forward primer) and amplifies a desired template.

A template is not particularly limited to a specific one and can be appropriately selected in accordance with an object to be detected. For example, it is possible to use, as the template, a polynucleotide (e.g., a DNA or an RNA) derived from any of the following: body fluids such as blood, lymph, snivel, sputum, urine, feces, and ascites; tissues such as skin, a mucous membrane, various internal organs and a bone; cleaning liquids with which a nasal cavity, a bronchus, skin, various organs, a bone, and the like have been cleaned; a plant; a microorganism; and the like. It is a matter of course that an aspect of the present invention is not limited to these templates.

The first primer has a region in which the double strand is formed by the first primer and the third polynucleotide sequence of the first probe and a region in which the double strand is formed by the first primer and the template.

The region of the first primer in which region the double strand is formed by the first primer and the third polynucleotide sequence of the first probe can be designed as a polynucleotide that is substantially complementary or complementary to the third polynucleotide sequence (described earlier). Note that since a description of a specific arrangement of the third polynucleotide sequence has already been given in detail, a specific arrangement of the region of the first primer in which region the double strand is formed by the first primer and the third polynucleotide sequence of the first probe will also be understandable from the description.

The region of the first primer in which region the double strand is formed by the first primer and the template can be appropriately designed in accordance with an object to be detected. That is, the region of the first primer in which region the double strand is formed by the first primer and the template can be designed as a polynucleotide that is substantially complementary or complementary to the template, and an arrangement of that region is not limited to a specific one.

The second primer only needs to be a primer with which a polynucleotide that is extended from the first primer forms a double strand, and an arrangement of the second primer is not limited to a specific one. A complementary strand of the polynucleotide that is extended from the first primer is extended from the second primer.

The second primer only needs to be capable of amplifying a desired template by being paired with the first primer. The second primer, whose arrangement is not limited to a specific one, is preferably arranged as in the case of the first primer (described earlier). In this case, the sample for the PCR reaction preferably contains a second probe which loses at least one bulge structure in a case where a double strand is formed by the second probe and the second primer and which forms the at least one bulge structure by being dissociated from the double strand formed by the second probe and the second primer.

The arrangement allows emission of a signal not only by the first probe but also by the second probe and thus allows detection of a PCR with higher accuracy.

More specifically, it is preferable that the second probe have a fourth polynucleotide sequence and a fifth polynucleotide sequence which form a double strand with each other by use of nucleotides different from a nucleotide forming the bulge structure and that the second probe have a sixth polynucleotide sequence with which a part of the second primer forms a double strand.

In this case, it is preferable that the sixth polynucleotide sequence include at least a part of the fourth polynucleotide sequence or the fifth polynucleotide sequence.

Further, it is preferable that a relational expression "$Tm_3>Tm_4$" where a melting temperature of the double strand formed by the sixth polynucleotide sequence and the second primer is $Tm_3$ and a melting temperature of the double strand formed by the fourth polynucleotide sequence and the fifth polynucleotide sequence is $Tm_4$ be satisfied. It is more preferable that a relational expression "$Tm_1>Tm_2>$signal measurement temperature" be satisfied. Note that a signal measurement temperature is not particularly limited to a specific one and can be, for example, 25° C. or 30° C.

The second primer, the second probe, the fourth polynucleotide sequence, the fifth polynucleotide sequence, and the sixth polynucleotide sequence can be arranged as in the case of the first primer, the first probe, the first polynucleotide sequence, the second polynucleotide sequence, and the third polynucleotide sequence, respectively.

Since respective arrangements of the first primer, the first probe, the first polynucleotide sequence, the second polynucleotide sequence, and the third polynucleotide sequence, i.e., the second primer, the second probe, the fourth polynucleotide sequence, the fifth polynucleotide sequence, and the sixth polynucleotide sequence, respectively, have already been described in the section [2-1. First probe], a description thereof is omitted here.

Note that the second primer, the second probe, the fourth polynucleotide sequence, the fifth polynucleotide sequence, and the sixth polynucleotide sequence only need to have respective specific arrangements that have already been described in the section [2-1. First probe]. The first primer and the second primer, the first probe and the second probe, the first polynucleotide sequence and the fourth polynucleotide sequence, the second polynucleotide sequence and the fifth polynucleotide sequence, or the third polynucleotide sequence and the sixth polynucleotide sequence may have arrangements that are perfectly identical to each other or different from each other.

A bulge structure-binding molecule only needs to emit a signal by binding to a bulge structure, and an arrangement of the bulge structure-binding molecule is not limited to a specific one.

The bulge structure-binding molecule is preferably made of, for example, a substance that by binding to a bulge structure, (i) emits fluorescence, (ii) shifts a wavelength of emitted fluorescence, or (iii) quenches fluorescence. Detection of such fluorescence makes it possible to easily detect a bulge structure. Note that it is also possible to use, as the bulge structure-binding molecule, a substance that is obtained by labeling, with a substance that is capable of emitting a signal (e.g., a fluorescent substance), a substance that is incapable of emitting a signal.

Specific examples of the bulge structure-binding molecule include a naphthyridine ring-containing compound.

The naphthyridine ring-containing compound which binds to a bulge structure (particularly preferably, a cytosine bulge structure and a thymine bulge structure) emits intense fluorescence. Detection of this fluorescence makes it possible to conveniently detect a bulge structure (i.e., how the PCR reaction progresses).

Further, the naphthyridine ring-containing compound does not inhibit an enzyme such as a DNA polymerase for use in the PCR reaction. Thus, the sample which contains the naphthyridine ring-containing compound can be subjected to the PCR reaction as it is.

For example, in a reaction container, the sample for the PCR reaction is prepared, and a naphthyridine ring-containing compound is mixed with the sample in advance. Before the PCR reaction is started, fluorescence of the sample is measured in advance. Then, the sample is subjected to the PCR reaction as it is. In a case where fluorescence of the sample is measured with time as the PCR reaction progresses, it is possible to detect a bulge structure.

Specific examples of the naphthyridine ring-containing compound include a 2,7-diaminonaphthyridine derivative represented by the following formula (1):

[Chem. 1]

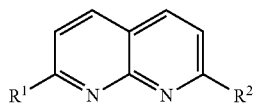
(1)

wherein $R^1$ and $R^2$ each independently represent a primary amine residue, a secondary amine residue, or a tertiary amine residue.

Examples of the primary amine residue include —NH$_2$. Examples of the secondary amine residue include —NH(CH$_2$)NH$_2$, —NH(CH$_2$)$_2$NH$_2$, —NH(CH)$_2$NH(CH$_3$), and the like. Examples of the tertiary amine residue include —N(CH$_3$)(CH$_2$)$_2$NH$_2$, and the like.

In the arrangement, it is preferable that at least one of $R_1$ and $R_2$ be the secondary amine residue, and it is more preferable that $R_1$ and $R_2$ be each the secondary amine residue. With the arrangement, the 2,7-diaminonaphthyridine derivative which includes the secondary amine residue allows more stable binding between the bulge structure-binding molecule and the bulge structure.

Specific examples of the 2,7-diaminonaphthyridine derivative include 2,7-diamino-1,8-naphthyridine represented by the following formula (2):

[Chem. 2]

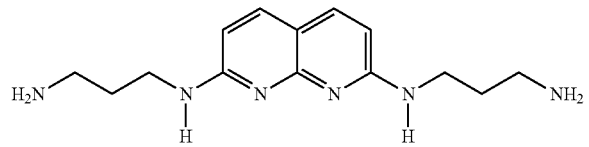
(2)

2,7-diamino-1,8-naphthyridine which binds to a bulge structure shifts an absorption maximum wavelength of emitted fluorescence and emits, at the shifted absorption maximum wavelength, fluorescence having a high intensity. This makes it possible to highly sensitively and specifically detect the bulge structure. Specifically, in a 10 mM sodium phosphate buffer solution (pH 7.0), 2,7-diamino-1,8-naphthyridine alone emits fluorescence at an absorption maximum of 376 nm, and 2,7-diamino-1,8-naphthyridine which binds to a cytosine bulge structure emits fluorescence at the absorption maximum which is shifted to 396 nm.

The naphthyridine ring-containing compound (e.g., a 2,7-diaminonaphthyridine derivative, 2,7-diamino-1,8-naphthyridine) only needs to be synthesized by a conventionally known method. For example, the naphthyridine ring-containing compound only needs to be synthesized by the method disclosed in "Japanese Patent Application Publication, Tokukai, No. 2004-262827".

Other specific examples of the naphthyridine ring-containing compound include a compound represented by the following formula (3):

[Chem. 3]

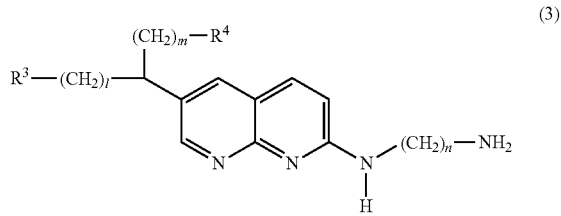
(3)

wherein $R^3$ and $R^4$ each independently represent a hydrogen atom or an amino group; and l, m, and n each independently represent a natural number of 1 to 6.

Other specific examples of the bulge structure-binding molecule include a compound represented by the following formula (4):

[Chem. 4]

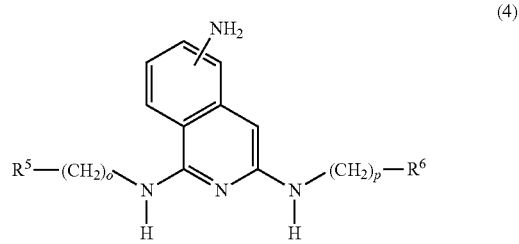
(4)

wherein $R^5$ and $R^6$ each independently represent a hydrogen atom or an amino group; and o and p each independently represent a natural number of 1 to 6.

The PCR method of the present embodiment is preferably arranged such that the sample (described earlier) further contains a competitor primer. The arrangement makes it possible to highly sensitively discriminate between templates that differ in base sequence. Thus, the PCR method of the present embodiment can be used for, for example, detection of an SNP.

An outline of a function of the competitor primer will be described with reference to (a) of FIG. 21.

Figure 21:
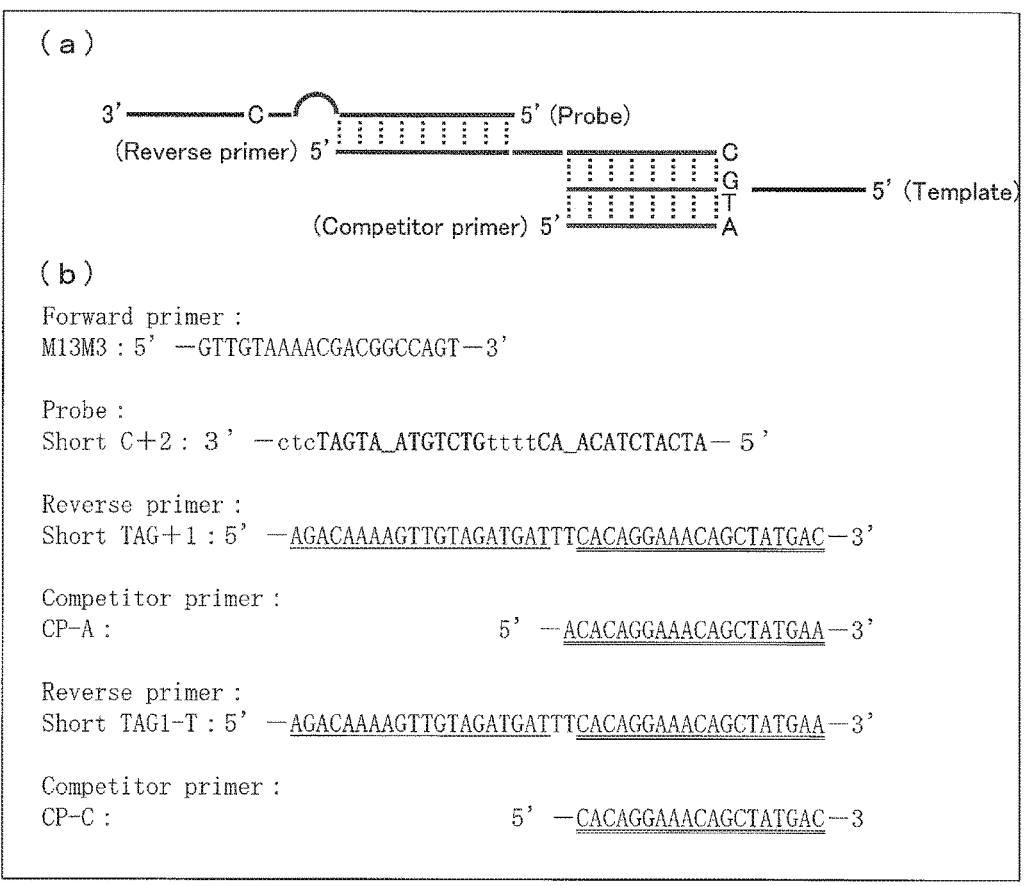
FIG. 21 illustrates respective structures of a probe (Short C+2 (SEQ ID NO: 20)), primers (M13M3 (SEQ ID NO: 1), Short TAG+1 (SEQ ID NO: 14), and Short TAG1-T (SEQ ID NO: 23)), and competitor primers (CP-A (SEQ ID NO: 22) and CP-C (SEQ ID NO: 24)) that were used in a further example of an aspect of the present invention.

According to the PCR method of the present embodiment, the sample can contain the first primer ("REVERSE PRIMER" in (a) of FIG. 21), the second primer (not illustrated), the first probe ("PROBE" in (a) of FIG. 21), the template, and the competitor primer.

(a) of FIG. 21 shows, as an example of the template, a template that has a single nucleotide polymorphism of "G" or "T". In this case, for example, a primer in which a nucleotide with which a nucleotide at a place in the template at which place the template has the single nucleotide polymorphism forms a double strand is "C" can be selected as the first primer, and a primer in which a nucleotide with which the nucleotide at the place in the template at which place the template has the single nucleotide polymorphism forms a double strand is "A" can be selected as the competitor primer.

In a case where the nucleotide at the place in the template at which place the template has the single nucleotide polymorphism is "G", the first primer and the template can more preferentially form a double strand than the competitor primer and the template. As a result, the PCR reaction in which the first primer is used preferentially occurs. The probe which has lost a partner with which the probe forms a double strand is dissociated in the PCR reaction solution so as to form a bulge structure. The bulge structure-binding molecule binds to the bulge structure, so that a signal (e.g., fluorescence) is emitted.

Meanwhile, in a case where the nucleotide at the place in the template at which place the template has the single nucleotide polymorphism is "T", the competitor primer and the template can more preferentially form a double strand than the first primer and the template. As a result, the PCR reaction in which the competitor primer is used preferentially occurs. In this case, the probe, which does not lose a partner with which the probe forms a double strand, is not dissociated in the PCR reaction solution so as to form a bulge structure. That is, no signal (e.g., fluorescence) is emitted.

Note that it can also be confirmed, by subjecting a product of the PCR reaction to electrophoresis and observing an amplified DNA, whether the first primer or the competitor primer, or each of the first primer and the competitor primer has appropriately functioned as a primer.

As described earlier, it is determined by a type of a gene sequence whether a signal is emitted. Therefore, the PCR method of the present embodiment can be suitably used for, for example, detection of an SNP.

Next, a specific arrangement of the competitor primer will be described.

The competitor primer at least has a seventh polynucleotide sequence that corresponds to a region of the first primer in which region a double strand is formed by the first primer and the template and at least one nucleotide (hereinafter referred to as a "nucleotide A") is replaced with another nucleotide (hereinafter referred to as a "nucleotide B").

The nucleotides A and B (described earlier) each form a double strand with a different nucleotide of a different genotype belonging to a genetic polymorphism (e.g., an SNP). That is, the nucleotide A forms a double strand with a DNA sequence of one of genotypes, and the nucleotide B forms a double strand with a DNA sequence of the other of the genotypes. For example, in (a) of FIG. 21, the nucleotide A corresponds to "C", and the nucleotide B corresponds to "A".

The number of nucleotides of the competitor primer is not particularly limited and only needs to be appropriately designed in accordance with the arrangement of the first primer and/or the arrangement of the template.

The seventh polynucleotide has nucleotides B whose number is not particularly limited and can be a desired one. For example, the seventh polynucleotide may have 1 to 10 nucleotide(s) B, 1 to 5 nucleotide(s) B, 1 to 3 nucleotide(s) B, 1 or 2 nucleotide(s) B, or 1 nucleotide B. From the viewpoint of detecting an SNP with higher accuracy, the seventh polynucleotide preferably has fewer nucleotides B.

A position of a nucleotide B in the seventh polynucleotide is not particularly limited and can be a desired one. For example, the nucleotide B may be located at a 5' end of the seventh polynucleotide, at any position between the 5' end of the seventh polynucleotide and a 3' end of the seventh polynucleotide, or at the 3' end of the seventh polynucleotide. From the viewpoint of detecting an SNP with higher accuracy, the nucleotide B is preferably located at the 3' end of the seventh polynucleotide.

The competitor primer is preferably arranged such that at least one nucleotide (e.g., 1 to 5, or 1 to 3 nucleotide(s)) (specifically, at least one nucleotide with which the template is capable of forming a double strand) is further attached to the 5' end of the seventh polynucleotide.

Assume that the number of nucleotides in the region of the first primer in which region the double strand is formed by the first primer and the template and the number of nucleotides in a region of the competitor primer in which region a double strand is formed by the competitor primer and the template are identical. In this case, as the number of cycles of the PCR reaction increases, the first primer, which is not supposed to be used for the PCR reaction, is used for the PCR reaction, so that a false positive signal is emitted. Meanwhile, the above arrangement of the competitor primer makes it possible to prevent emission of such a false positive signal.

The above description regards the competitor primer as a primer that competes with the first primer. Note, however, that in an arrangement in which the second probe is used, the competitor primer can be arranged to serve as a primer that competes with the first primer, a primer that competes with the second primer, or a primer that competes with each of the first primer and the second primer.

The PCR method of the present embodiment includes the step of: subjecting, to the PCR reaction, the sample containing: the primer set, the template, the probe(s), and the bulge structure-binding molecule, each of which has been described earlier, or the sample containing: the primer set, the template, the probe(s), the bulge structure-binding molecule, and the competitor primer, each of which has been described earlier.

Further, the PCR method of the present embodiment may include, after the above step, the step of detecting a signal (e.g., fluorescence) derived from the sample.

The step of subjecting the sample to the PCR reaction can be carried out by use of a commercially available PCR reaction device in accordance with a well-known protocol.

In at least the step of detecting the signal derived from the sample, the sample has a pH preferably of not less than 5, more preferably of not less than 6, and still more preferably of not less than 6.5. The pH has an upper limit preferably of not more than 9, more preferably of not more than 8, and still more preferably of not more than 7.5. The pH which is not less than 5 and not more than 9 makes a DNA stable. Thus, the bulge structure-binding molecule satisfactorily binds to a bulge structure. This makes it possible to satisfactorily detect the signal.

The probes contained in the sample each have a concentration that is preferably 0.5 time to 1.0 time, more preferably 0.75 time to 1.0 time, and still more preferably 1.0 time a concentration of the primer which forms a double strand. The arrangement makes it possible to satisfactorily detect the signal.

The bulge structure-binding molecule contained in the sample has a concentration that is preferably 2 times to 40 times, more preferably 5 times to 20 times, and still more preferably 10 times a concentration of a probe to which the bulge structure-binding molecule binds. The arrangement makes it possible to satisfactorily detect the signal.

A specific arrangement of the step of detecting the signal derived from the sample only needs to be appropriately selected in accordance with a type of the signal.

For example, detection of fluorescence that is emitted in response to binding of the bulge structure-binding molecule to a bulge structure is not limited provided that the fluorescence is detectable. Note, however, that the fluorescence has a wavelength preferably of 400 nm to 480 nm, and more preferably of 430 nm to 460 nm. The fluorescence which has a wavelength of 400 nm to 480 nm makes it possible to clearly discriminate between (a) fluorescence that is emitted in a case where the bulge structure-binding molecule (e.g., 2,7-diamino-1,8-naphthyridine) does not bind to the bulge structure and (b) fluorescence that is emitted in a case where the bulge structure-binding molecule binds to the bulge structure.

A PCR kit of the present embodiment for causing a primer set including a first primer and a second primer to amplify a template, the PCR kit includes: a first probe which loses at least one bulge structure in a case where a double strand is formed by the first probe and the first primer and which forms the at least one bulge structure by being dissociated from the double strand formed by the first probe and the first primer; and a bulge structure-binding molecule which emits a signal by binding to the at least one bulge structure.

Since the first probe and the bulge structure-binding molecule have already been specifically described, a description thereof is omitted here.

The PCR kit of the present embodiment may further include the primer set including the first primer and the second primer.

Since the primer set has already been specifically described, a description thereof is omitted here.

A PCR kit of the present embodiment may further include: a second probe which loses at least one bulge structure in a case where a double strand is formed by the second probe and the second primer and which forms the at least one bulge structure by being dissociated from the double strand formed by the second probe and the second primer.

Since the second probe has already been specifically described, a description thereof is omitted here.

A PCR kit of the present embodiment may further include: a competitor primer having a seventh polynucleotide sequence that corresponds to a region of the first primer in which region a double strand is formed by the first primer and the template and at least one nucleotide is replaced with another nucleotide.

Since the competitor primer has already been specifically described, a description thereof is omitted here.

A PCR kit of the present embodiment may further include a reagent and/or an instrument, e.g., a PCR-related reagent and/or a PCR-related instrument (a DNA polymerase, dNTP, a PCR buffer, a PCR tube, etc.), an amplified nucleic acid purification reagent and/or an amplified nucleic acid purification instrument, a reagent and/or a buffer solution for stably preserving a DNA fragment, and/or a reagent and/or a buffer for stably preserving the bulge structure-binding molecule.

<1. Electrophoresis Analysis and Fluorescence Analysis of PCR Reaction Product (Study on Type of Bulge Structure)>

A PCR reaction was carried out by use of two types of combinations of a reverse primer, a forward primer, and a probe, PCR reaction products were detected by electrophoresis, and a test of how a fluorescence intensity is changed in accordance with an increase in PCR reaction product was carried out.

The following two combinations of a reverse primer, a forward primer, and a probe were used for the PCR reaction. Further, pUC18 was used as a template for the PCR reaction, and 2,7-diamino-1,8-naphthyridine (DANP) was used as a bulge structure-binding molecule.

(A. Combination 1)

Forward primer (M13M3):
(SEQ ID NO 1)
5'-GTTGTAAAACGACGGCCAGT-3',

Reverse primer (C-bulge 1):
(SEQ ID NO 2)
5'-TCATTACAAAAGTAGATGATTTCACAGGAAACAGCTATGAC-3', Probe (C-probe 1):
(SEQ ID NO 3)
5'-ATCATCTACTTTTGTAATGATCTC-3'

(B. Combination 2)

Forward primer (M13M3),

Reverse primer (T-bulge 1):
(SEQ ID NO 4)
5'-GCTATCAAAAGAAGCTATCTATTTCACAGGAAACAGCTATGAC-3', Probe (T-probe 1):
(SEQ ID NO 5)
5'-ATAGATAGCTTCTTTTGATAGCTTCTATCTC-3'

A relationship among the arrangements will be more specifically described with reference to FIG. 2.

Figure 2:
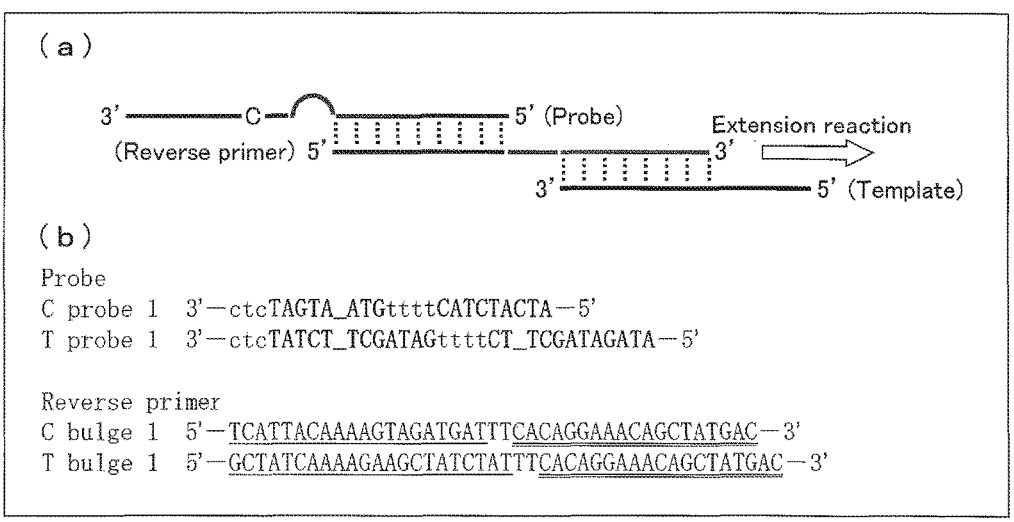
FIG. 2 illustrates respective structures of probes (C probe 1 (SEQ ID NO: 3) and T probe 1 (SEQ ID NO: 5)) and primers (C bulge 1 (SEQ ID NO: 2 and T bulge 1 (SEQ ID NO: 4) that were used in an example of an aspect of the present invention.

As illustrated in (b) of FIG. 2, the probe of the present example is designed to form therein a double strand between base sequences indicated by a "boldfaced capital letter". Note that a part indicated by an "underline" is a region in which there exists no base that forms a double strand with a complementary strand "C" or "T", which forms a bulge structure.

That is, the probe (C-probe 1) of the present example is a probe that forms therein a cytosine bulge structure at one site, and the probe (T-probe 1) of the present example is a probe that forms therein thymine bulge structures at two sites.

As illustrated in (b) of FIG. 2, the reverse primer of the present example is designed to form a double strand with the probe in a base sequence indicated by a "single underline", and to form a double strand with the template in a base sequence indicated by a "double underline".

The double strand which is formed by the reverse primer (C-bulge 1) and the probe (C-probe 1) had a melting temperature ($Tm_1$) of 48.2° C., and the double strand which is formed in the probe (C-probe 1) had a melting temperature ($Tm_2$) of 42.4° C.

Meanwhile, the double strand which is formed by the reverse primer (T-bulge 1) and the probe (T-probe 1) had a melting temperature ($Tm_1$) of 54.7° C., and the double strand which is formed in the probe (T-probe 1) had a melting temperature ($Tm_2$) of 45.3° C.

Note that a melting temperature was calculated by use of OligoCalc (lnc50 mM $Na^+$, "available at the website www-.basic.northwestern.edu at biotools/oligocalc.html").

As a reaction solution, used was a reaction solution (40 μL in total) containing the forward primer having a concentration of 0.5 μM, the reverse primer having a concentration of 0.5 μM, the probe having a concentration of 0.5 μM, the bulge structure-binding molecule having a concentration of 5 μM, and the template of 100 pg/μL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

The reaction solution was taken as the PCR reaction program progresses. The taken reaction solution was subjected to electrophoresis analysis (specifically, Native PAGE (8% polyacrylamide gel, SYBR gold staining)) and fluorescence analysis. Electrophoresis analysis was carried out by use of a commercially available electrophoretic device and a commercially available gel. Fluorescence analysis was carried out by use of BERTHOLD Mithras LB940 manufactured by Berthold Technologies (excitation wavelength: 400 nm, emission wavelength: 450 nm).

Figure 3:
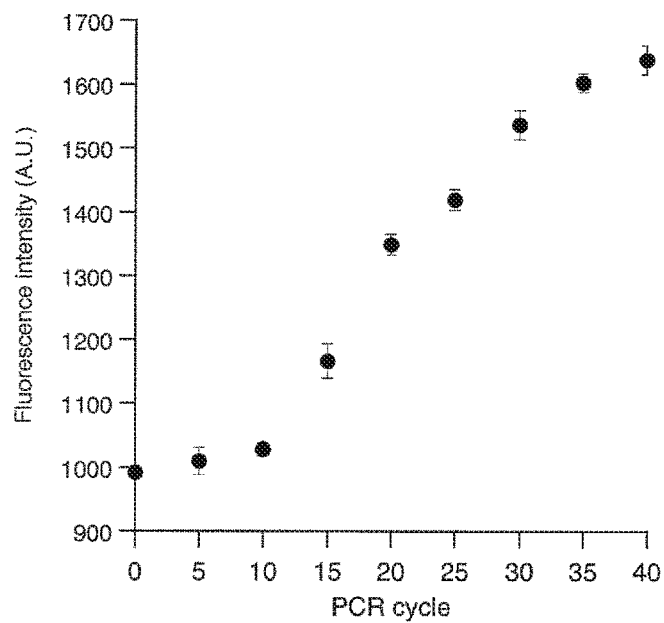
FIG. 3 is a graph showing a result of fluorescence analysis carried out in the example of an aspect of the present invention.
Figure 4:
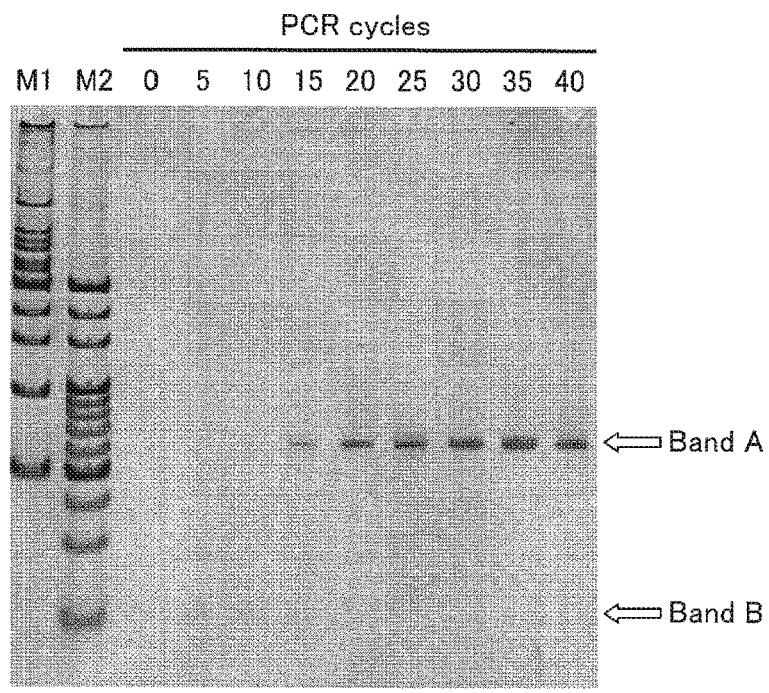
FIG. 4 is a photograph showing a result of electrophoresis analysis carried out in the example of an aspect of the present invention.
Figure 5:
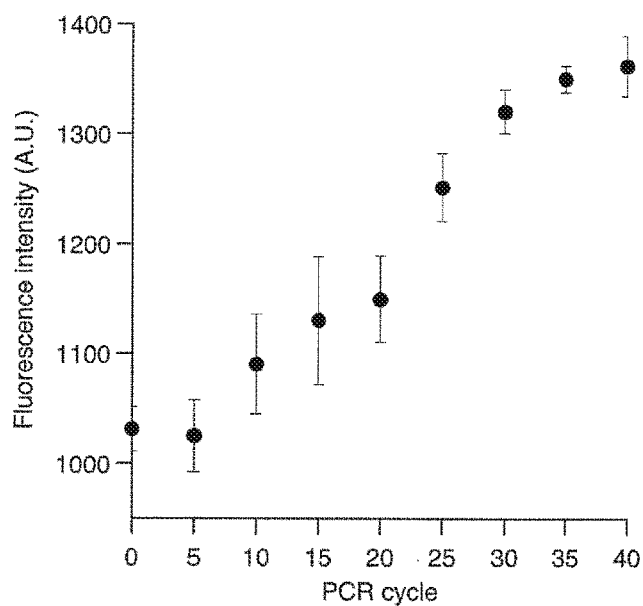
FIG. 5 is a graph showing a result of fluorescence analysis carried out in the example of an aspect of the present invention.
Figure 6:
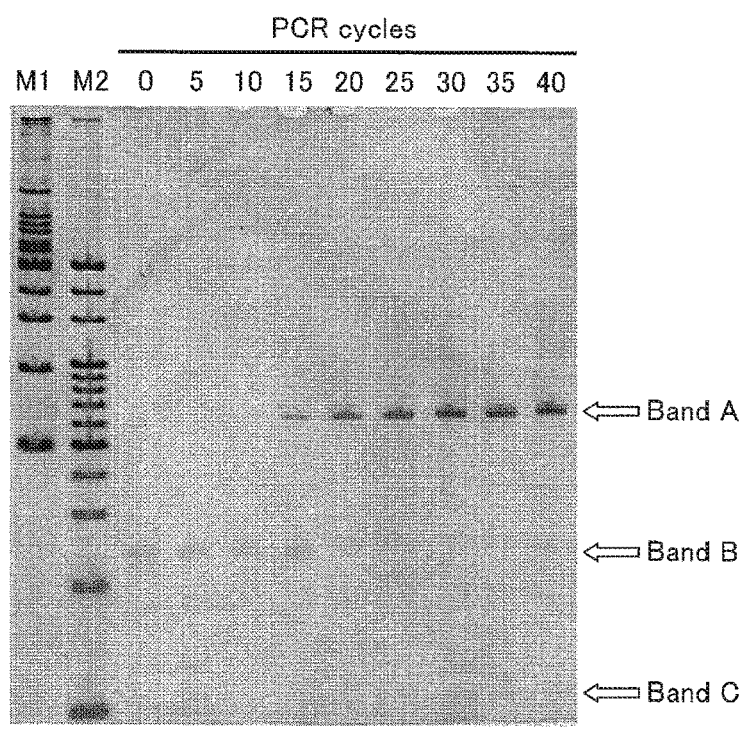
FIG. 6 is a photograph showing a result of electrophoresis analysis carried out in the example of an aspect of the present invention.

FIGS. 3 and 4 show test results of (A. Combination 1). FIGS. 5 and 6 show test results of (B. Combination 2). Note that in FIGS. 4 and 6, a band indicated by "Band A" corresponds to a PCR product, a band indicated by "Band B" corresponds to a complex of the probe and the reverse primer, and a band indicated by "Band C" corresponds to the probe which forms therein the double strand. Note also that in FIGS. 4 and 6, "M1" indicates a ladder marker of 20 bp, and "M2" indicates a ladder marker of 100 bp.

As shown in FIGS. 4 and 6, it is revealed that regardless of what kind of bulge structure is formed by the probe, as the PCR reaction progresses, the complex of the probe and the reverse primer has a smaller amount, and the PCR product and the probe which forms therein the double strand each have a larger amount.

As shown in FIGS. 3 and 5, regardless of what kind of bulge structure is formed by the probe, as the PCR reaction progresses, the PCR reaction solution has a higher fluorescence intensity.

<2. Electrophoresis Analysis and Fluorescence Analysis of PCR Reaction Product (Study on Number of Bulge Structures)>

In the example of <1> (described earlier), the probe that forms therein a cytosine bulge structure at one site was used to carry out the test. In the present test, a probe that forms therein cytosine bulge structures at two sites was used to carry out a test so as to examine how a fluorescence intensity is changed.

A reverse primer, a forward primer, and a probe that were used for a PCR reaction have the respective sequences below. Further, pUC18 was used as a template for the PCR reaction, and 2,7-diamino-1,8-naphthyridine (DANP) was used as a bulge structure-binding molecule.

```
Forward primer (M13M3):

Reverse primer (M13RV-TAG + 1):
                                        (SEQ ID NO 6)
5'-GTAGATGATAATACGTCACTTCACAGGAAACAGCTATGAC-3', Probe (HP-3-C + 2):
                                        (SEQ ID NO 7)
5'-GTGACGTATTATCATCTACAACTTTTGTCTGTAATGATCTC-3'
```

A relationship among the arrangements will be more specifically described with reference to FIG. 7.

Figure 7:
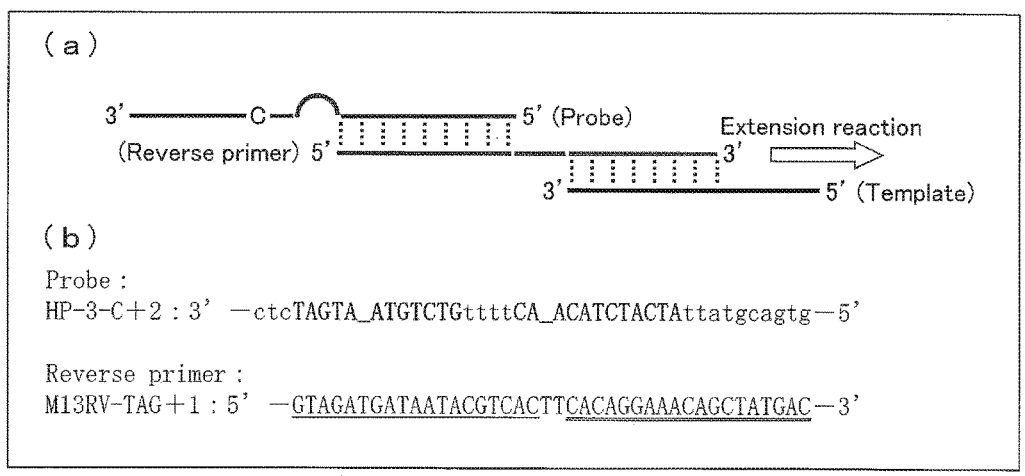
FIG. 7 illustrates respective structures of a probe (HP-3-C+2 (SEQ ID NO: 7)) and a primer (M13RV-TAG+1 (SEQ ID NO: 9) that were used in another example of an aspect of the present invention.

As illustrated in (b) of FIG. 7, the probe of the present example is designed to form therein a double strand between base sequences indicated by a "boldfaced capital letter". Note that a part indicated by an "underline" is a region in which there exists no base that forms a double strand with a complementary strand "C", which forms a bulge structure. That is, the probe of the present example is a probe that forms therein cytosine bulge structures at two sites.

As illustrated in (b) of FIG. 7, the reverse primer of the present example is designed to form a double strand with the probe in a base sequence indicated by a "single underline", and to form a double strand with the template in a base sequence indicated by a "double underline".

As a reaction solution, used was a reaction solution (40 μL in total) containing the forward primer having a concentration of 0.5 μM, the reverse primer having a concentration of 0.5 μM, the probe having a concentration of 0.5 μM, the bulge structure-binding molecule having a concentration of 5 μM, and the template of 100 pg/μL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, electrophoresis analysis and fluorescence analysis were carried out as in the case of the example of <1> (described earlier).

Figure 8:
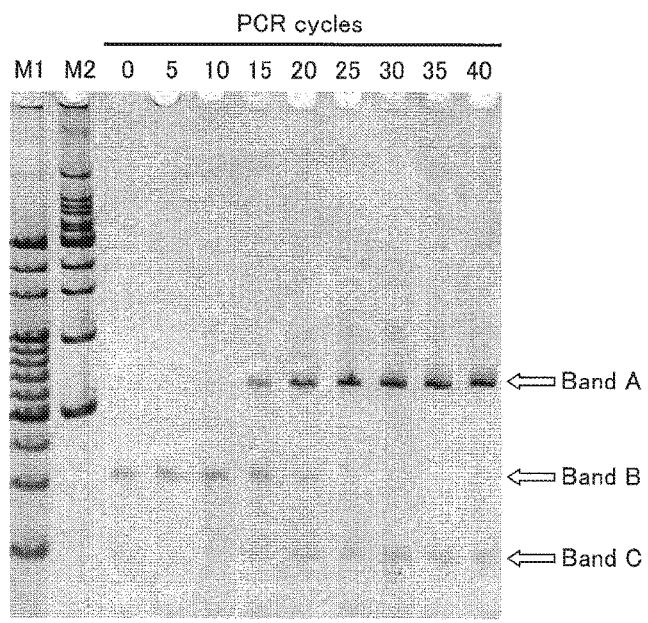
FIG. 8 is a photograph showing a result of electrophoresis analysis carried out in the another example of an aspect of the present invention.
Figure 9:
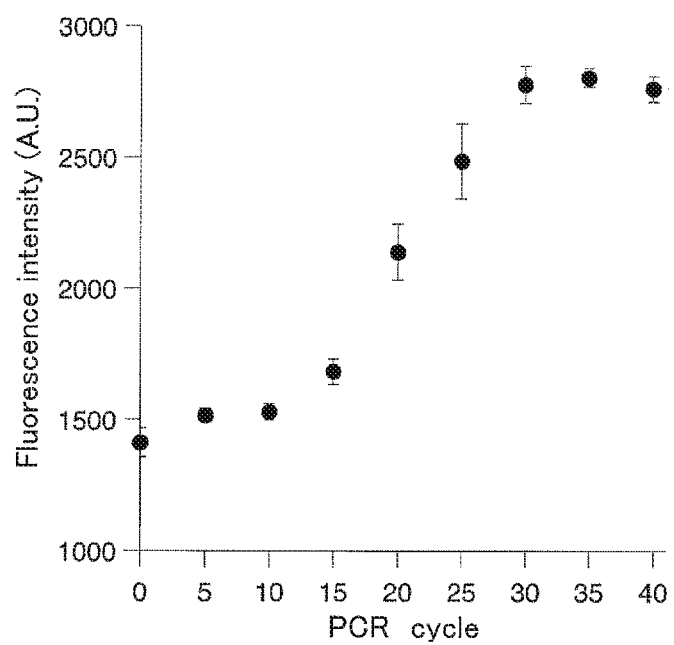
FIG. 9 is a graph showing a result of fluorescence analysis carried out in the another example of an aspect of the present invention.

FIGS. 8 and 9 show test results.

As shown in FIG. 8, it is revealed that as the PCR reaction progresses, a complex of the probe and the reverse primer has a smaller amount, and a PCR product and the probe which forms therein the double strand each have a larger amount. As shown in FIG. 9, as the PCR reaction progresses, the PCR reaction solution has a higher fluorescence intensity.

Further, a result of comparison between FIGS. 3 and 9 reveals that formation of more bulge structures in the probe further increases PCR detection sensitivity.

<3. Examination of Designs for Reverse Primer and Probe-1>

As the reverse primer, the following four types of primers were prepared.

Note that the following four types of reverse primers differ in length of a base sequence in which a double strand is formed by a reverse primer and the probe (HP-3-C+2).

Note that the double strand which is formed by the probe and the primer "M13RV-TAG" had a melting temperature ($Tm_1$) of 46.9° C., the double strand which is formed by the probe and the primer "M13RV-TAG+1" had a melting temperature ($Tm_1$) of 50.9° C., the double strand which is formed by the probe and the primer "M13RV-TAG+2" had a melting temperature ($Tm_1$) of 52.3° C., and the double strand which is formed by the probe and the primer "M13RV-TAG+3" had a melting temperature ($Tm_1$) of 53.4° C.

Note that a double strand which is formed in the probe (HP-3-C+2) had a melting temperature ($Tm_2$) of 42.8° C. (calculated by mfold).

Note that a melting temperature was calculated by use of OligoCalc (Inc50 mM Na$^+$, "available at the website www-.basic.northwestern.edu at biotools/oligocalc.html").

Reverse primer (M13RV-TAG):
(SEQ ID NO 8)
5'-TAGATGATAATACGTCACTTCACAGGAAACAGCTATGAC-3', Reverse primer (M13RV-TAG + 1):
(SEQ ID NO 9)
5'-GTAGATGATAATACGTCACTTCACAGGAAACAGCTATGAC-3', Reverse primer (M13RV-TAG + 2):
(SEQ ID NO 10)
5'-TGTAGATGATAATACGTCACTTCACAGGAAACAGCTATGAC-3', Reverse primer (M13RV-TAG + 3):
(SEQ ID NO 11)
5'-TTGTAGATGATAATACGTCACTTCACAGGAAACAGCTATGAC-3'

A relationship among the arrangements will be more specifically described with reference to FIG. 10.

Figure 10:
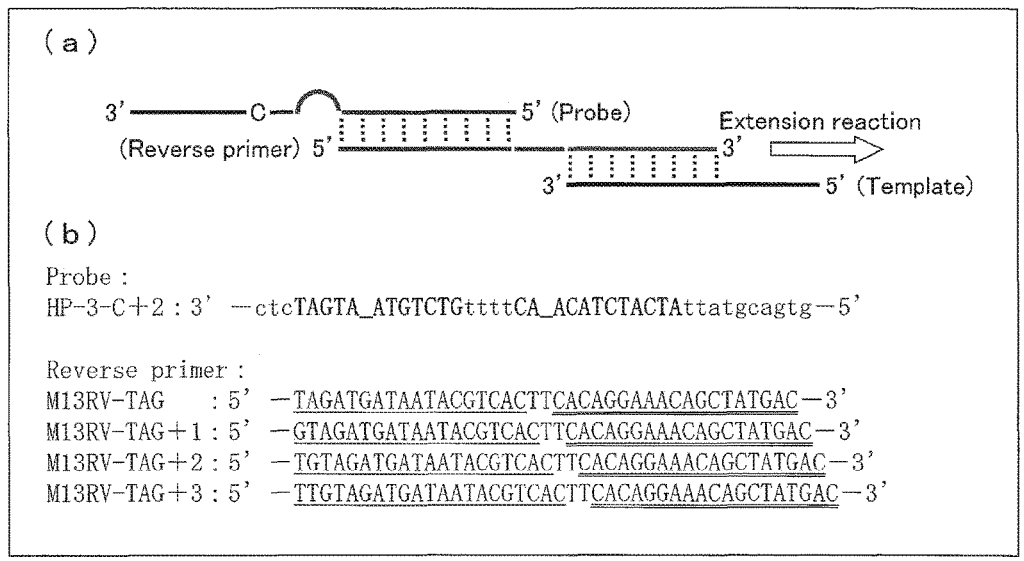
FIG. 10 illustrates respective structures of a probe (HP-3-C+2 (SEQ ID NO: 7)) and primers (M13RV-TAG (SEQ ID NO: 8), M13RV-TAG+1 (SEQ ID NO: 9), M13RV-TAG+2 (SEQ ID NO: 10), and M13RV-TAG+3 (SEQ ID NO: 11)) that were used in still another example of an aspect of the present invention.

As illustrated in (b) of FIG. 10, the probe of the present example is designed to form therein the double strand between base sequences indicated by a "boldfaced capital letter". Note that a part indicated by an "underline" is a region in which there exists no base that forms a double strand with a complementary strand "C", which forms a bulge structure. That is, the probe of the present example is a probe that forms therein cytosine bulge structures at two sites.

As illustrated in (b) of FIG. 10, the reverse primers of the present example are each designed to form the double strand with the probe in a base sequence indicated by a "single underline", and to form a double strand with a template in a base sequence indicated by a "double underline".

A PCR reaction was carried out by use of the four types of reverse primers (described earlier), a forward primer (M13M3), the probe (HP-3-C+2), pUC18 as the template, and 2,7-diamino-1,8-naphthyridine (DANP) as a bulge structure-binding molecule.

Specifically, as a reaction solution, used was a reaction solution (40 µL in total) containing the forward primer having a concentration of 0.5 µM, the reverse primer having a concentration of 0.5 µM, the probe having a concentration of 0.5 µM, the bulge structure-binding molecule having a concentration of 5 µM, and the template of 100 pg/µL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, fluorescence analysis was carried out as in the case of the example of <1> (described earlier).

Figure 11:
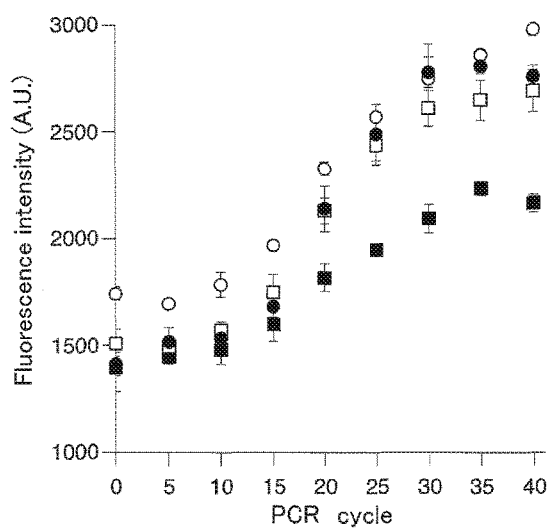
FIG. 11 is a graph showing a result of fluorescence analysis carried out in the still another example of an aspect of the present invention.

FIG. 11 shows a test result. Note that the test result shown in FIG. 11 reveals that the ranking of fluorescence intensities, from highest to lowest, is "M13RV-TAG", "M13RV-TAG+1", "M13RV-TAG+2", and "M13RV-TAG+3" at 40 "PCR cycle"s.

As shown in FIG. 11, any of the reverse primers caused an increase in fluorescence intensity of the PCR reaction solution as the PCR reaction progressed. Note, however, that "M13RV-TAG+1" had the highest PCR detection sensitivity of the reverse primers.

<4. Examination of Designs for Reverse Primer and Probe-2>

As the reverse primer, the following eight types of primers were prepared. Further, a new probe was prepared.

Note that the following eight types of reverse primers differ in length of a base sequence in which a double strand is formed by a reverse primer and the new probe (Short C+2).

Note that the double strand which is formed by the new probe and the primer "Short TAG+3" had a melting temperature ($Tm_1$) of 54.7° C., the double strand which is formed by the new probe and the primer "Short TAG+2" had a melting temperature ($Tm_1$) of 53.4° C., the double strand which is formed by the new probe and the primer "Short TAG+1" had a melting temperature ($Tm_1$) of 50.2° C., the double strand which is formed by the new probe and the primer "Short TAG-0" had a melting temperature ($Tm_1$) of 48.9° C., the double strand which is formed by the new probe and the primer "Short TAG-1" had a melting temperature ($Tm_1$) of 44.8° C., the double strand which is formed by the new probe and the primer "Short TAG-2" had a melting temperature ($Tm_1$) of 42.6° C., the double strand which is formed by the new probe and the primer "Short TAG-3" had a melting temperature ($Tm_1$) of 37.9° C., and the double strand which is formed by the new probe and the primer "Short TAG-4" had a melting temperature ($Tm_1$) of 35.3° C.

Note that a double strand which is formed in the probe (Short C+2) had a melting temperature ($Tm_2$) of 42.8° C. (calculated by mfold).

Note that a melting temperature was calculated by use of OligoCalc (Inc50 mM Na$^+$, "available at the website www-.basic.northwestern.edu at biotools/oligocalc.html").

Reverse primer (Short TAG + 3):
(SEQ ID NO 12)
5'-ACAGACAAAAGTTGTAGATGATTTCACAGGAAACAGCTATGAC-3'

Reverse primer (Short TAG + 2):
(SEQ ID NO 13)
5'-CAGACAAAAGTTGTAGATGATTTCACAGGAAACAGCTATGAC-3', Reverse primer (Short TAG + 1):
(SEQ ID NO 14)
5'-AGACAAAAGTTGTAGATGATTTCACAGGAAACAGCTATGAC-3', Reverse primer (Short TAG-0):
(SEQ ID NO 15)
5'-GACAAAAGTTGTAGATGATTTCACAGGAAACAGCTATGAC-3', Reverse primer (Short TAG-1):
(SEQ ID NO 16)
5'-ACAAAAGTTGTAGATGATTTCACAGGAAACAGCTATGAC-3', Reverse primer (Short TAG-2):
(SEQ ID NO 17)
5'-CAAAAGTTGTAGATGATTTCACAGGAAACAGCTATGAC-3', Reverse primer (Short TAG-3):
(SEQ ID NO 18)
5'-AAAAGTTGTAGATGATTTCACAGGAAACAGCTATGAC-3', Reverse primer (Short TAG-4):
(SEQ ID NO 19)
5'-AAAGTTGTAGATGATTTCACAGGAAACAGCTATGAC-3', Probe (Short C + 2):
(SEQ ID NO 20)
5'-ATCATCTACAACTTTTGTCTGTAATGATCTC-3'

A relationship among the arrangements will be more specifically described with reference to FIG. 12.

Figure 12:
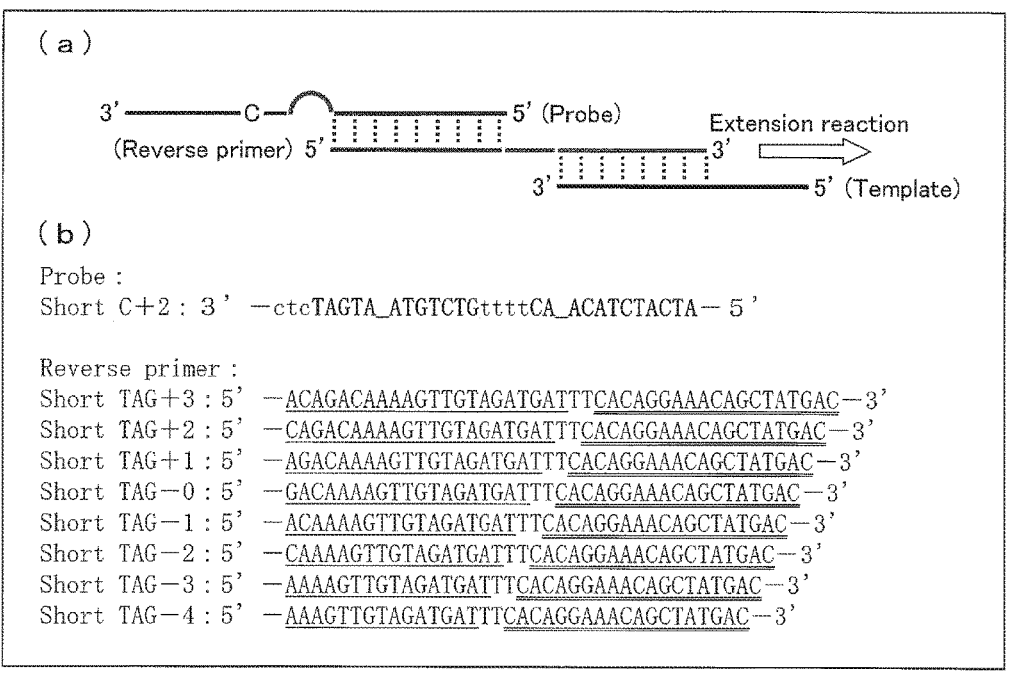
FIG. 12 illustrates respective structures of a probe (Short C+2 (SEQ ID NO: 20)) and primers (Short TAG+3 (SEQ ID NO: 12), Short TAG+2 (SEQ ID NO: 13), Short TAG+1 (SEQ ID NO: 14), Short TAG-0 (SEQ ID NO: 15), Short TAG-1 (SEQ ID NO: 16), Short TAG-2 (SEQ ID NO: 17), Short TAG-3 (SEQ ID NO: 18), and Short TAG-4 (SEQ ID NO: 19)) that were used in a further example of an aspect of the present invention.

As illustrated in (b) of FIG. 12, the probe of the present example is designed to form therein the double strand between base sequences indicated by a "boldfaced capital letter". Note that a part indicated by an "underline" is a region in which there exists no base that forms a double strand with a complementary strand "C", which forms a bulge structure. That is, the probe of the present example is a probe that forms therein cytosine bulge structures at two sites.

As illustrated in (b) of FIG. 12, the reverse primers of the present example are each designed to form the double strand with the probe in a base sequence indicated by a "single underline", and to form a double strand with a template in a base sequence indicated by a "double underline".

A PCR reaction was carried out by use of the eight types of reverse primers (described earlier), a forward primer (M13M3), the probe (Short C+2), pUC18 as the template, and 2,7-diamino-1,8-naphthyridine (DANP) as a bulge structure-binding molecule.

Specifically, as a reaction solution, used was a reaction solution (40 μL in total) containing the forward primer having a concentration of 0.5 μM, the reverse primer having a concentration of 0.5 μM, the probe having a concentration of 0.5 μM, the bulge structure-binding molecule having a concentration of 5 μM, and the template of 100 pg/μL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, fluorescence analysis was carried out as in the case of the example of <1> (described earlier).

Figure 13:
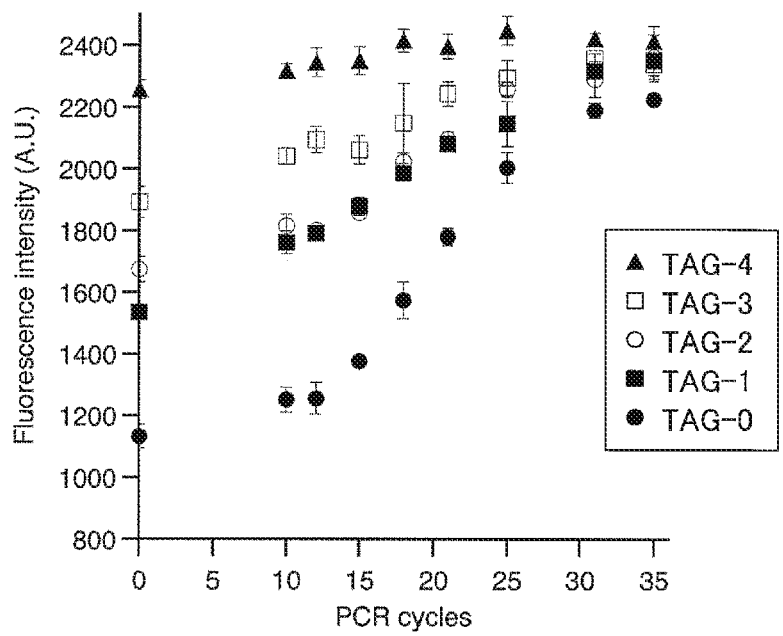
FIG. 13 is a graph showing a result of fluorescence analysis carried out in the further example of an aspect of the present invention.
Figure 14:
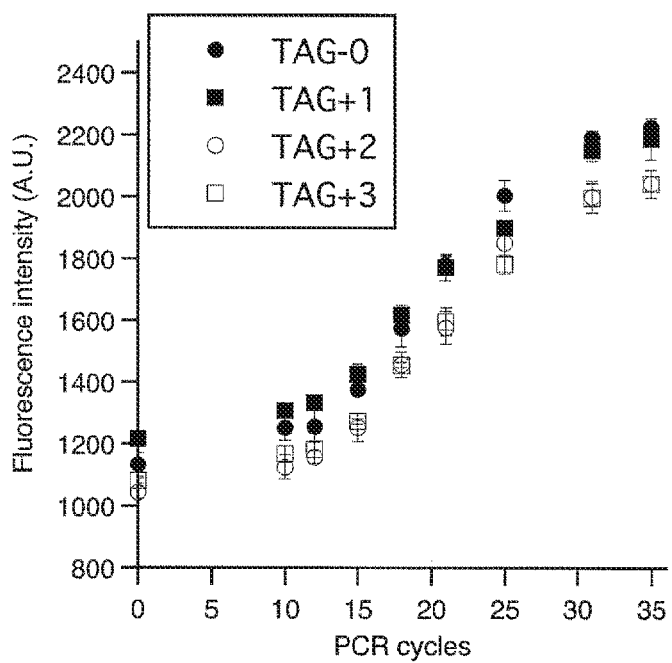
FIG. 14 is a graph showing a result of fluorescence analysis carried out in a further example of an aspect of the present invention.

FIGS. 13 and 14 show test results.

As is clear from FIGS. 13 and 14, it is revealed that a combination of the probe and the reverse primer which combination satisfies a relational expression "$Tm_1 > Tm_2$" is large in amount of change in fluorescence intensity per unit PCR cycle. This shows that the combination of the probe and the reverse primer which combination satisfies the relational expression "$Tm_1 > Tm_2$" further increases PCR detection sensitivity.

<5. Examination of Concentration of Template>

A PCR reaction was carried out by changing a concentration of a template, and a test of how a fluorescence intensity is changed in accordance with an increase in PCR reaction product was carried out.

The PCR reaction was carried out by use of a reverse primer (M13RV-TAG+1), a forward primer (M13M3), a probe (HP-3-C+2), pUC18 as the template, and 2,7-diamino-1,8-naphthyridine (DANP) as a bulge structure-binding molecule.

Specifically, as a reaction solution, used was a reaction solution (40 μL in total) containing the forward primer having a concentration of 0.5 μM, the reverse primer having a concentration of 0.5 μM, the probe having a concentration of 0.5 μM, the bulge structure-binding molecule having a concentration of 5 μM, and the template of 1.8 μM, 0.18 μM, 18 μM, 1.8 μM, 0.18 μM, 18 fM, or 1.8 fM.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, fluorescence analysis was carried out as in the case of the example of <1> (described earlier).

Figure 15:
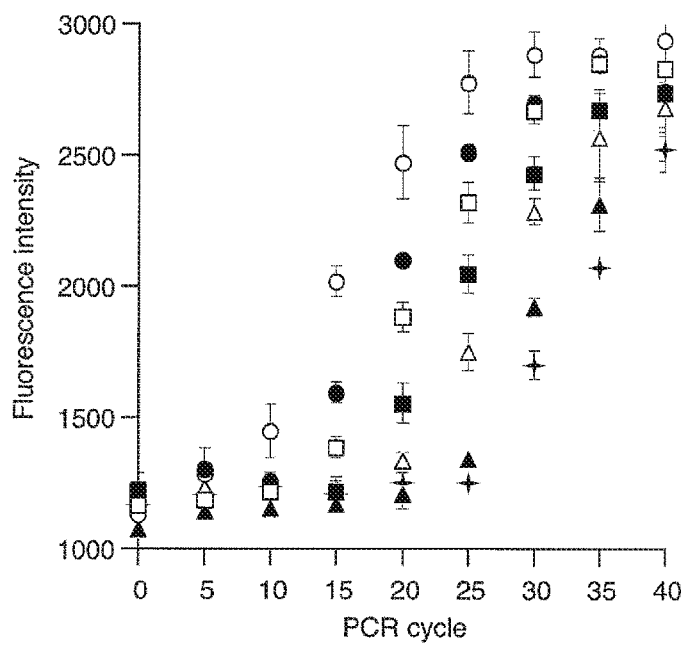
FIG. 15 is a graph showing a result of fluorescence analysis carried out in a further example of an aspect of the present invention by changing a concentration of a template.
Figure 16:
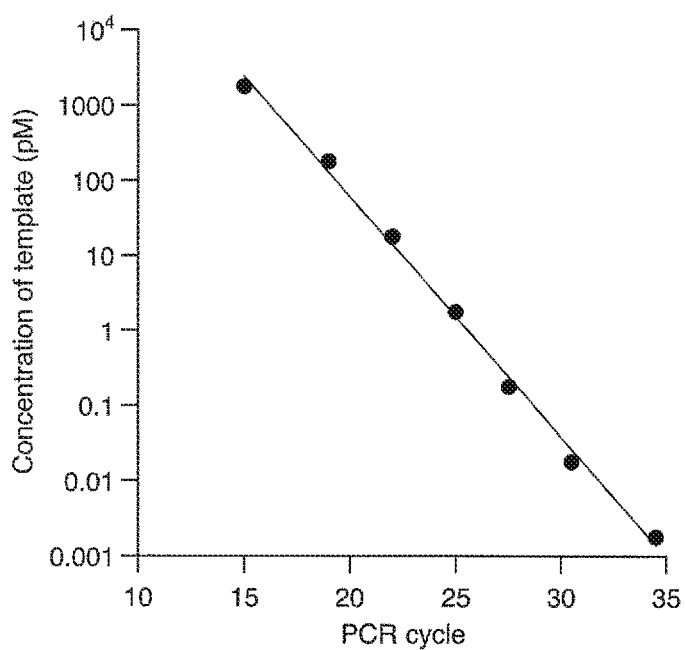
FIG. 16 is a graph on which concentrations of a template were plotted against the number of PCR cycles in the further example of an aspect of the present invention.

FIG. 15 shows a result of measurement of the fluorescence intensity in each PCR cycle. FIG. 16 shows data obtained by plotting a template concentration against the number of PCR cycles in accordance with the test result of FIG. 15 at a fluorescence intensity of 2000 (A.U.).

As shown in FIG. 16, the data obtained by plotting the template concentration against the number of PCR cycles is substantially linear. This reveals that the PCR method of the present embodiment can be suitably used as quantitative PCR.

<6. Examination of Polymerase>

A PCR reaction was carried out by use of a plurality of kinds of polymerases, and a test of how a fluorescence intensity is changed in accordance with an increase in PCR reaction product was carried out.

The PCR reaction was carried out by use of a reverse primer (M13RV-TAG, M13RV-TAG+1, M13RV-TAG+2, or M13RV-TAG+3), a forward primer (M13M3), a probe (HP-3-C+2), pUC18 as a template, and 2,7-diamino-1,8-naphthyridine (DANP) as a bulge structure-binding molecule.

As a polymerase, Taq polymerase (manufactured by QUIAGEN), which is a PolI-type PCR enzyme, or KOD-FX polymerase (manufactured by TOYOBO CO., LTd.), which is an α-type PCR enzyme, was used.

Note that Taq polymerase, which is a PolI-type PCR enzyme, is an enzyme that is derived from Bacteria, has no 3'→5' Exonuclease activity, and has 5'→3' Exonuclease activity and TdT activity.

Meanwhile, KOD-FX polymerase, which is an α-type PCR enzyme, is an enzyme that is derived from Archaea, has 3'→5' Exonuclease activity, and has neither 5'→3' Exonuclease activity nor TdT activity.

Specifically, as a reaction solution, used was a reaction solution (40 μL in total) containing the forward primer having a concentration of 0.5 μM, the reverse primer having a concentration of 0.5 μM, the probe having a concentration of 0.5 μM, the bulge structure-binding molecule having a concentration of 5 μM, and the template of 100 pg/μL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, fluorescence analysis was carried out as in the case of the example of <1> (described earlier).

Figure 17:
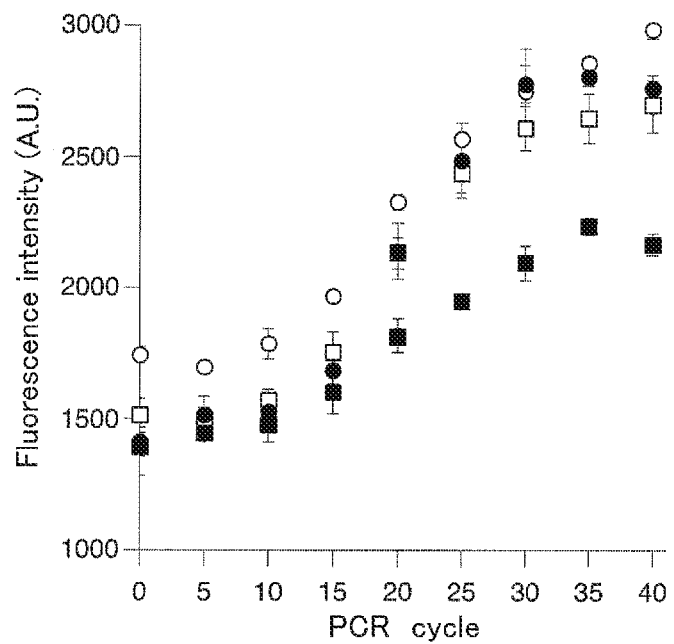
FIG. 17 is a graph showing a result of fluorescence analysis carried out in a further example of an aspect of the present invention by use of Taq polymerase.
Figure 18:
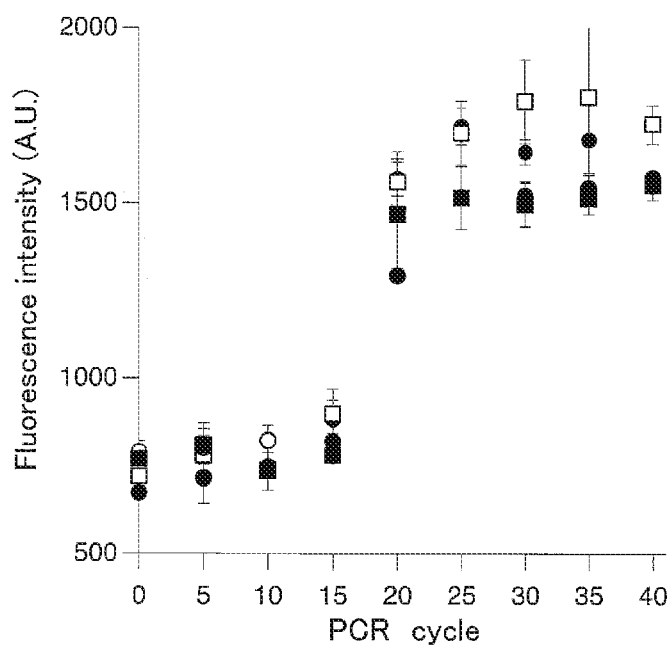
FIG. 18 is a graph showing a result of fluorescence analysis carried out in the further example of an aspect of the present invention by use of KOD-FX polymerase.

FIG. 17 shows a test result of Taq polymerase, and FIG. 18 shows a test result of KOD-FX polymerase.

Note that the test result shown in FIG. 17 reveals that the ranking of fluorescence intensities, from highest to lowest, is "M13RV-TAG", "M13RV-TAG+1", "M13RV-TAG+2", and "M13RV-TAG+3" at 35 "PCR cycle"s. Note also that the test result shown in FIG. 18 reveals that the ranking of fluorescence intensities, from highest to lowest, is "M13RV-TAG+2", "M13RV-TAG+3", "M13RV-TAG+1", and "M13RV-TAG" at 35 "PCR cycle"s.

As is clear from FIGS. 17 and 18, it is revealed that also in a case where a different type of enzyme is used, the PCR reaction solution has a higher fluorescence intensity as the PCR reaction progresses.

<7. Test on Case of Using Forward Primer and Reverse Primer Each Forming Double Strand with Probe>

A PCR reaction was carried out by use of two types of combinations of a reverse primer, a forward primer, and a probe, PCR reaction products were detected by electrophoresis, and a test of how a fluorescence intensity is changed in accordance with an increase in PCR reaction product was carried out.

The following two combinations of a reverse primer, a forward primer, and a probe were used for the PCR reaction. Further, pUC18 was used as a template for the PCR reaction, and 2,7-diamino-1,8-naphthyridine (DANP) was used as a bulge structure-binding molecule.

(A. Combination 3)

```
Forward primer (Short TAG1-M13M3):
                                          (SEQ ID NO 21)
5'-AGACAAAAGTTGTAGATGATTTCAGTTGTAAAACGACGGCCAGT-3',
```

Reverse primer (Short TAG+1):
Probe (Short C+2)
(B. Combination 4)
Forward primer (M13M3):
Reverse primer (Short TAG+1):
Probe (Short C+2)

A relationship among the arrangements will be more specifically described with reference to FIG. 19.

Figures 19, 20:
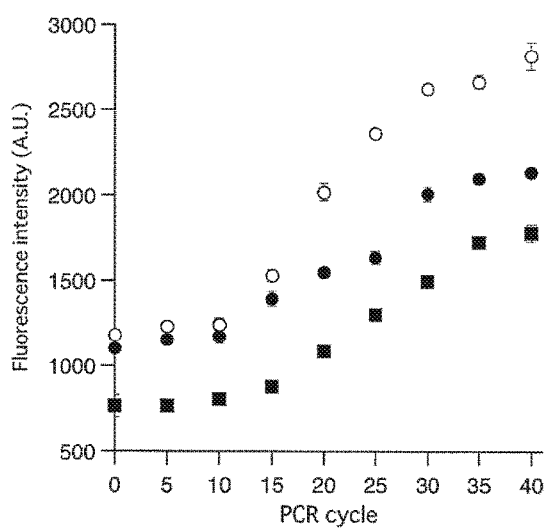
FIG. 19 illustrates respective structures of a probe (Short C+2 (SEQ ID NO: 20) and primers (Short TAG+1 (SEQ ID NO: 14), and Short tag1-M13M3 (SEQ ID NO: 21)) that were used in a further example of an aspect of the present invention.
FIG. 20 is a graph showing a result of fluorescence analysis carried out in the further example of an aspect of the present invention.

As illustrated in FIG. 19, the probe of the present example is designed to form therein a double strand between base sequences indicated by a "boldfaced capital letter". Note that a part indicated by an "underline" is a region in which there exists no base that forms a double strand with a complementary strand "C", which forms a bulge structure. That is, the probe of the present example is a probe that forms therein cytosine bulge structures at two sites.

As illustrated in FIG. 19, the reverse primer and the forward primer of the present example are each designed to form a double strand with the probe in a base sequence indicated by a "single underline", and to form a double strand with the template in a base sequence indicated by a "double underline".

As a reaction solution for the case of each of the above (Combination 3) and (Combination 4), used was a reaction solution (40 µL in total) containing the forward primer having a concentration of 0.5 µM, the reverse primer having a concentration of 0.5 µM, the probe having a concentration of 0.5 µM, the bulge structure-binding molecule having a concentration of 5 µM, and the template of 100 pg/µL.

Further, as another reaction solution for the case of the above (Combination 3), used was a reaction solution (40 µL in total) containing the forward primer having a concentration of 0.5 µM, the reverse primer having a concentration of 0.5 µM, the probe having a concentration of 1 µM, the bulge structure-binding molecule having a concentration of 5 µM, and the template of 100 pg/µL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 40 times. Note that the PCR reaction was specifically carried out by use of TP600 PCR Thermal Cycler (TAKARA).

Next, fluorescence analysis was carried out as in the case of the example of <1> (described earlier).

FIG. 20 shows a test result. Note that the test result shown in FIG. 20 reveals that the ranking of fluorescence intensities, from highest to lowest, is "a case where the probe having a concentration of 1 was used in Combination 3", "a case where the probe having a concentration of 0.5 was used in Combination 4", and "a case where the probe having a concentration of 0.5 was used in Combination 3" at 40 "PCR cycle"s.

As shown in FIG. 20, it is revealed that in a case where the probe has a constant concentration, as compared with an arrangement in which the probe is capable of binding to only the forward primer, an arrangement in which the probe is capable of binding to both the forward primer and the reverse primer greatly decreases in fluorescence intensity (i.e., background) before a start of the PCR reaction.

Further, as shown in FIG. 20, it is revealed that as compared with a case where the probe has a lower concentration, a case where the probe has a higher (e.g., two times higher) concentration is slightly higher in fluorescence intensity (i.e., background) before the start of the PCR reaction, but an amount of change in fluorescence intensity (i.e., a difference between the fluorescence intensity before the PCR reaction and the fluorescence intensity after the PCR reaction) is made greater (approximately 1.5 times greater). This shows that the case where the probe has a higher concentration further increases PCR detection sensitivity.

<8. Discrimination of Gene Polymorphism by Use of Competitor Primer>

A PCR reaction was carried out by use of two types of combinations of a reverse primer, a forward primer, and a probe, and two types of combinations of a reverse primer, a forward primer, a competitor primer, and a probe (four types of combinations in total), PCR reaction products were detected by electrophoresis, and a test of how a fluorescence intensity is changed in accordance with an increase in PCR reaction product was carried out.

A specific arrangement of the four types of combinations is described below. Further, pUC18 (a template whose allele is "G", a template whose allele is "T", or a mixture of (a) a template whose allele is "G" and (b) a template whose allele is "T") was used as a template for the PCR reaction, and 2,7-diamino-1,8-naphthyridine (DANP) was used as a bulge structure-binding molecule.

(A. Combination 5)
Forward primer (M13M3):
Reverse primer (Short TAG+1):
Probe (Short C+2):

```
        Competitor primer (CP-A):
                                          (SEQ ID NO 22)
          5'-ACACAGGAAACAGCTATGAA-3'
```

(B. Combination 6)
Forward primer (M13M3):
Reverse primer (Short TAG+1):
Probe (Short C+2)
(C. Combination 7)

```
Forward primer (M13M3):

Reverse primer (Short TAG1-T):
                                          (SEQ ID NO 23)
5'-AGACAAAAGTTGTAGATGATTTCACAGGAAACAGCTATGAA-3', Probe (Short C + 2):

Competitor primer (CP-C):
                                          (SEQ ID NO 24)
5'-CACAGGAAACAGCTATGAC-3'
```

(D. Combination 8)
Forward primer (M13M3):
Reverse primer (Short TAG1-T):
Probe (Short C+2)

A relationship among the arrangements will be more specifically described with reference to FIG. 21.

As illustrated in FIG. 21, the probe of the present example is designed to form therein a double strand between base sequences indicated by a "boldfaced capital letter". Note that a part indicated by an "underline" is a region in which there exists no base that forms a double strand with a complementary strand "C", which forms a bulge structure. That is, the probe of the present example is a probe that forms therein cytosine bulge structures at two sites.

As illustrated in FIG. 21, the reverse primer and the forward primer of the present example are each designed to form a double strand with the probe in a base sequence indicated by a "single underline", and to form a double strand with the template in a base sequence indicated by a "double underline".

Further, the reverse primer of the present example is designed to form a double strand with the template in a base sequence indicated by a "double underline". Note that as compared with the reverse primer (Short TAG+1), the competitor primer (CP-A) is larger, by one, in number of nucleotides each of which is capable of forming the double strand with the template (see "A" at the 5' end of the competitor primer (CP-A)).

As a reaction solution for each of the above (Combination 6) and (Combination 8), used was a reaction solution (40 µL in total) containing the forward primer having a concentration of 0.5 µM, the reverse primer having a concentration of 0.5 µM, the probe having a concentration of 0.5 µM, the bulge structure-binding molecule having a concentration of 5 µM, and the template of 100 pg/µL.

Meanwhile, as a reaction solution for each of the above (Combination 5) and (Combination 7), used was a reaction solution (40 µL in total) containing the forward primer having a concentration of 0.5 µM, the reverse primer having a concentration of 0.5 µM, the probe having a concentration of 0.5 µM, the competitor primer having a concentration of 0.5 µM, the bulge structure-binding molecule having a concentration of 5 µM, and the template of 100 pg/µL.

As a PCR reaction program, used was a PCR reaction program in which a denaturation reaction is carried out first at 95° C. for 2 minutes and then a cycle of reactions that are the denaturation reaction at 95° C. for 10 seconds, an annealing reaction at 55° C. for 30 seconds, and an extension reaction at 72° C. for 30 seconds is repeated 35 times. Note that the PCR reaction was specifically carried out by use of TP600 PCR Thermal Cycler (TAKARA).

Next, electrophoresis analysis and fluorescence analysis were carried out as in the case of the example of <1> (described earlier).

FIGS. 22 through 25 show test results.

Figure 24:
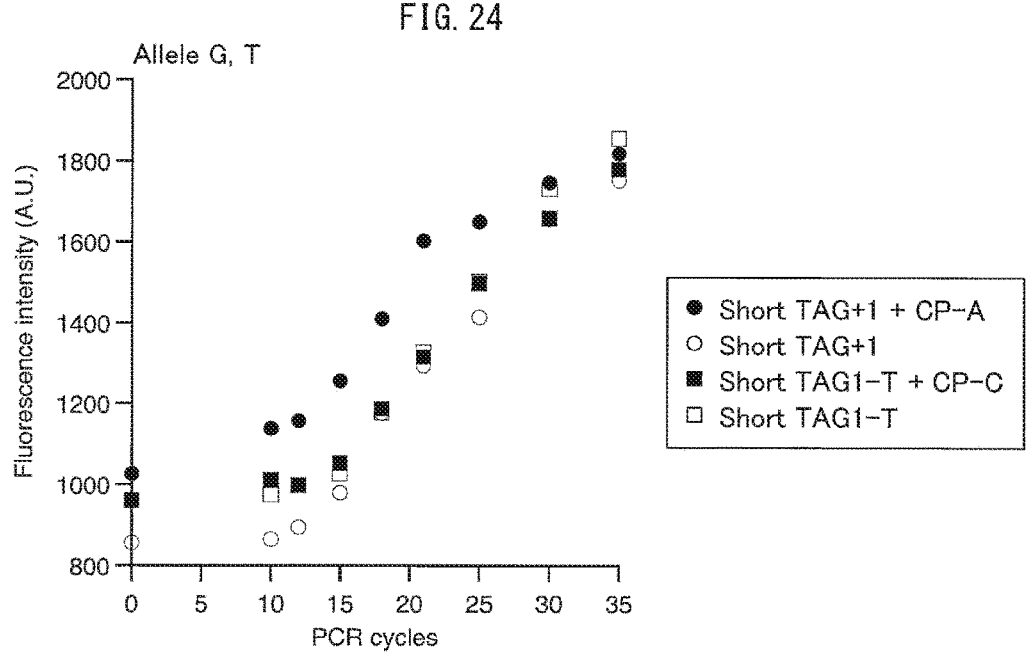
FIG. 24 is a graph showing a result of fluorescence analysis carried out in the further example of an aspect of the present invention by use of a mixture of (a) a template whose allele is "G" and (b) a template whose allele is "T".

Specifically, FIG. 22 shows a result of fluorescence analysis carried out by use of a template whose allele is "G". FIG. 23 shows a result of fluorescence analysis carried out by use of a template whose allele is "T". FIG. 24 shows a result of fluorescence analysis carried out by use of a mixture of (a) a template whose allele is "G" and (b) a template whose allele is "T".

Figure 25:
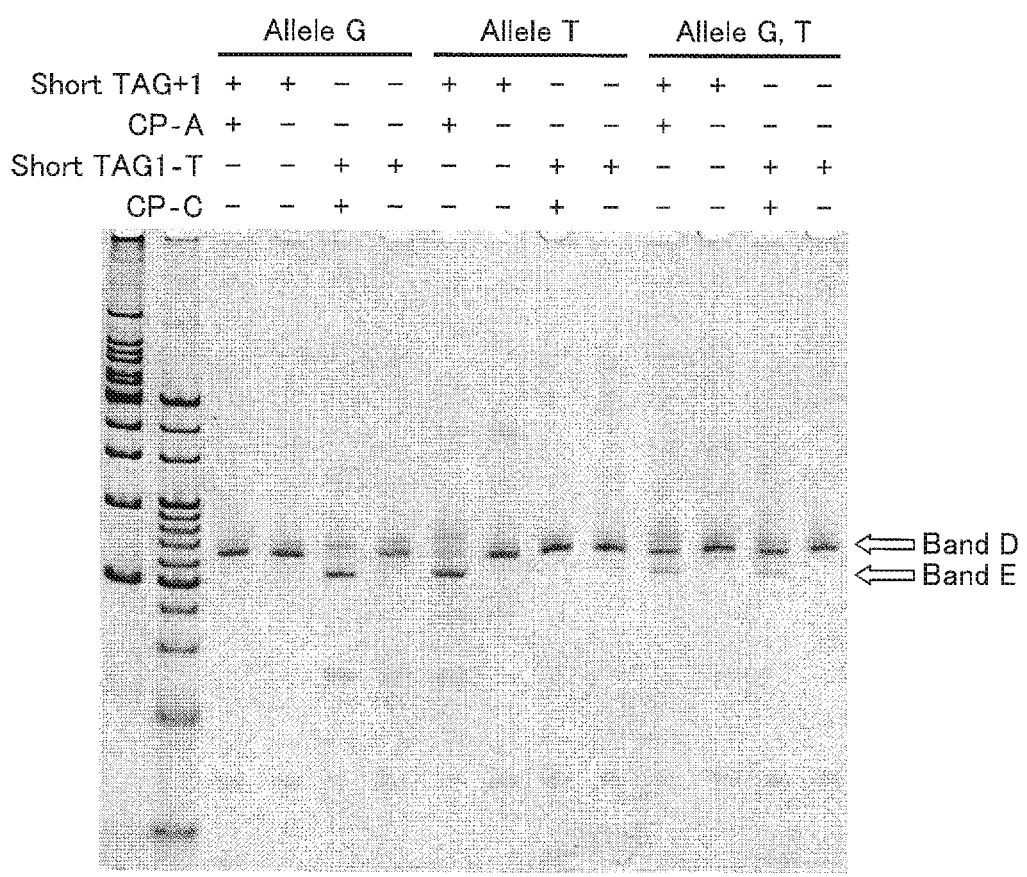
FIG. 25 is a photograph showing a result of electrophoresis analysis carried out in the further example of an aspect of the present invention.
Figure 26:
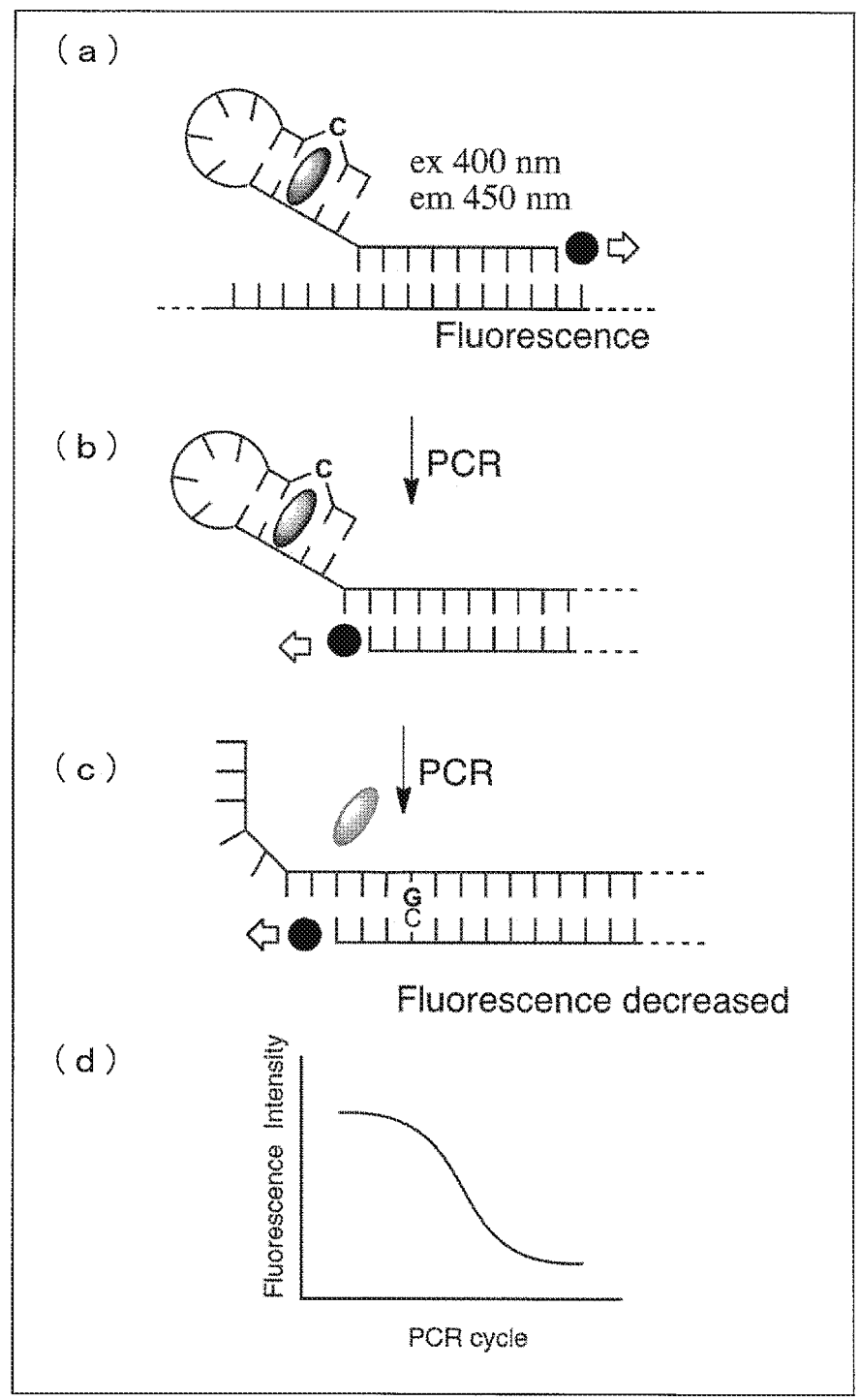
FIG. 26 illustrates a fundamental principle of a conventional technique.

FIG. 25 shows a result of electrophoresis analysis. Note that in FIG. 25, a band indicated by "Band D" corresponds to a PCR reaction product amplified by the reverse primer (Short TAG+1) or the reverse primer (Short TAG1-T) and the forward primer (M13M3), and a band indicated by "Band E" corresponds to a PCR reaction product amplified by the competitor primer (CP-A) or the competitor primer (CP-C) and the forward primer (M13M3).

FIGS. 22 through 25 reveal that use of the competitor primer makes it possible to highly sensitively discriminate between templates that differ in base sequence.

The present invention can be used for various PCRs (e.g., real time PCR, allele specific PCR, quantitative PCR, and reverse transcription (RT)-PCR).

The invention claimed is:

1. A PCR method comprising the step of:
subjecting a sample to a PCR reaction,
the sample containing:
   a primer set including a first primer and a second primer;
   a template amplified by the primer set;
   a first probe which loses at least one bulge structure in a case where a double strand is formed by the first probe and the first primer and which forms the at least one bulge structure by being dissociated from the double strand formed by the first probe and the first primer; and
   a bulge structure-binding molecule which emits a signal by binding to the at least one bulge structure.

2. The PCR method as set forth in claim 1, wherein:
the first probe has a first polynucleotide sequence and a second polynucleotide sequence which form a double strand with each other by use of nucleotides different from a nucleotide forming the at least one bulge structure, and the first probe has a third polynucleotide sequence with which a part of the first primer forms a double strand; and
the third polynucleotide sequence includes at least a part of the first polynucleotide sequence or the second polynucleotide sequence.

3. The PCR method as set forth in claim 2, wherein $Tm_1 > Tm_2$ where a melting temperature of the double strand formed by the third polynucleotide sequence and the first primer is $Tm_1$ and a melting temperature of the double strand formed by the first polynucleotide sequence and the second polynucleotide sequence is $Tm_2$.

4. The PCR method as set forth in claim 1, wherein the at least one bulge structure formed by the first probe comprises a plurality of bulge structures.

5. The PCR method as set forth in claim 1, wherein the sample further contains a second probe which loses at least one bulge structure in a case where a double strand is formed by the second probe and the second primer and which forms the at least one bulge structure by being dissociated from the double strand formed by the second probe and the second primer.

6. The PCR method as set forth in claim 5, wherein:
the second probe has a fourth polynucleotide sequence and a fifth polynucleotide sequence which form a double strand with each other by use of nucleotides different from a nucleotide forming the at least one bulge structure, and the second probe has a sixth polynucleotide sequence with which a part of the second primer forms a double strand; and
the sixth polynucleotide sequence includes at least a part of the fourth polynucleotide sequence or the fifth polynucleotide sequence.

7. The PCR method as set forth in claim 6, wherein $Tm_3 > Tm_4$ where a melting temperature of the double strand formed by the sixth polynucleotide sequence and the second primer is $Tm_3$ and a melting temperature of the double strand formed by the fourth polynucleotide sequence and the fifth polynucleotide sequence is $Tm_4$.

8. The PCR method as set forth in claim 5, wherein the at least one bulge structure formed by the second probe comprises a plurality of bulge structures.

9. The PCR method as set forth in claim 1, wherein the at least one bulge structure is a cytosine bulge structure or a thymine bulge structure.

10. The PCR method as set forth in claim 1, wherein the bulge structure-binding molecule is a naphthyridine ring-containing compound.

11. The PCR method as set forth in claim 1, wherein:
the sample further contains a competitor primer; and
the competitor primer has a seventh polynucleotide sequence that corresponds to a region of the first primer in which region a double strand is formed by the first primer and the template and at least one nucleotide is replaced with another nucleotide.

* * * * *